(12) United States Patent
Yip et al.

(10) Patent No.: US 6,896,697 B1
(45) Date of Patent: May 24, 2005

(54) INTRAVASCULAR STENT

(75) Inventors: Philip S. Yip, San Jose, CA (US); Santosh Prabhu, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 282 days.

(21) Appl. No.: 10/334,036

(22) Filed: Dec. 30, 2002

(51) Int. Cl.$^7$ .................................................. A61F 2/06
(52) U.S. Cl. .................................... 623/1.15; 623/1.16
(58) Field of Search .............................. 623/1.15–1.22, 623/1.27, 1.35

(56) References Cited

U.S. PATENT DOCUMENTS

| | | |
|---|---|---|
| 2,701,559 A | 2/1955 | Cooper |
| 3,105,492 A | 10/1963 | Jeckel |
| 3,657,744 A | 4/1972 | Ersek |
| 3,868,956 A | 3/1975 | Alfidi et al. |
| 3,993,078 A | 11/1976 | Bergentz et al. |
| 4,130,904 A | 12/1978 | Whalen |
| 4,140,126 A | 2/1979 | Choudhury |
| 4,159,719 A | 7/1979 | Haerr |
| 4,323,071 A | 4/1982 | Simpson et al. |
| 4,387,952 A | 6/1983 | Slusher |
| 4,503,569 A | 3/1985 | Dotter |
| 4,504,354 A | 3/1985 | George et al. |
| 4,512,338 A | 4/1985 | Balko et al. |
| 4,516,972 A | 5/1985 | Samson |
| 4,531,933 A | 7/1985 | Norton et al. |
| 4,553,545 A | 11/1985 | Maass et al. |
| 4,560,374 A | 12/1985 | Hammerslag |
| 4,580,568 A | 4/1986 | Gianturco |
| 4,616,652 A | 10/1986 | Simpson |
| 4,619,246 A | 10/1986 | Molgaard-Nielsen et al. |
| 4,649,922 A | 3/1987 | Wiktor |
| 4,650,466 A | 3/1987 | Luther |
| 4,655,771 A | 4/1987 | Wallsten |
| 4,665,918 A | 5/1987 | Garza et al. |
| 4,681,110 A | 7/1987 | Wiktor |
| 4,706,671 A | 11/1987 | Weinrib |
| 4,733,665 A | 3/1988 | Palmaz |
| 4,739,762 A | 4/1988 | Palmaz |
| 4,740,207 A | 4/1988 | Kreamer |
| 4,748,982 A | 6/1988 | Horzewski et al. |
| 4,760,849 A | 8/1988 | Kropf |
| 4,762,128 A | 8/1988 | Rosenbluth |
| 4,767,418 A | 8/1988 | Deininger et al. |
| 4,768,507 A | 9/1988 | Fischell et al. |
| 4,776,337 A | 10/1988 | Palmaz |
| 4,795,458 A | 1/1989 | Regan |

(Continued)

FOREIGN PATENT DOCUMENTS

| | | |
|---|---|---|
| EP | 0 221 570 A2 | 5/1987 |
| EP | 0 338 816 A2 | 10/1989 |
| EP | 0 364 787 A1 | 4/1990 |

(Continued)

OTHER PUBLICATIONS

Dotter, Charles T. *Transluminally Placed Coilspring Endarterial Tube Grafts, Investigative Radiology*, pp. 329–332, Sep./Oct. 1969.

(Continued)

*Primary Examiner*—David H. Willse
*Assistant Examiner*—Hieu Phan
(74) *Attorney, Agent, or Firm*—Fulwider Patton Lee & Utecht, LLP

(57) ABSTRACT

An intravascular stent assembly for implantation in a body vessel, such as a coronary artery, includes undulating circumferential rings having peaks on the proximal end and valleys on the distal end. Adjacent rings are coupled together between peaks on one ring and valleys on the proximally adjacent ring. To increase flexibility of the stent, the links do not couple all of the peaks on a ring to the proximally adjacent ring.

179 Claims, 11 Drawing Sheets

U.S. PATENT DOCUMENTS

| | | |
|---|---|---|
| 4,800,882 A | 1/1989 | Gianturco |
| 4,830,003 A | 5/1989 | Wolff et al. |
| 4,848,343 A | 7/1989 | Wallsten et al. |
| 4,856,516 A | 8/1989 | Hillstead |
| 4,870,966 A | 10/1989 | Dellon et al. |
| 4,877,030 A | 10/1989 | Beck et al. |
| 4,878,906 A | 11/1989 | Lindemann et al. |
| 4,886,062 A | 12/1989 | Wiktor |
| 4,887,997 A | 12/1989 | Okada |
| 4,892,539 A | 1/1990 | Koch |
| 4,893,623 A | 1/1990 | Rosenbluth |
| 4,907,336 A | 3/1990 | Gianturco |
| 4,913,141 A | 4/1990 | Hillstead |
| 4,921,479 A | 5/1990 | Grayzel |
| 4,922,905 A | 5/1990 | Strecker |
| 4,923,464 A | 5/1990 | DiPisa, Jr. |
| 4,943,346 A | 7/1990 | Mattelin |
| 4,950,227 A | 8/1990 | Savin et al. |
| 4,963,022 A | 10/1990 | Sommargren |
| 4,969,458 A | 11/1990 | Wiktor |
| 4,969,890 A | 11/1990 | Sugita et al. |
| 4,986,831 A | 1/1991 | King et al. |
| 4,988,356 A | 1/1991 | Crittenden et al. |
| 4,990,155 A | 2/1991 | Wilkoff |
| 4,994,071 A | 2/1991 | MacGregor |
| 4,998,539 A | 3/1991 | Delsanti |
| 5,002,560 A | 3/1991 | Machold et al. |
| 5,007,926 A | 4/1991 | Derbyshire |
| 5,015,253 A | 5/1991 | MacGregor |
| 5,019,085 A | 5/1991 | Hillstead |
| 5,019,090 A | 5/1991 | Pinchuk |
| 5,026,377 A | 6/1991 | Burton et al. |
| 5,034,001 A | 7/1991 | Garrison et al. |
| 5,035,706 A | 7/1991 | Giantureo et al. |
| 5,037,377 A | 8/1991 | Alonso |
| 5,037,392 A | 8/1991 | Hillstead |
| 5,037,427 A | 8/1991 | Harada et al. |
| 5,041,126 A | 8/1991 | Gianturco |
| 5,059,211 A | 10/1991 | Stack et al. |
| 5,061,273 A | 10/1991 | Yock |
| 5,061,275 A | 10/1991 | Wallsten et al. |
| 5,062,829 A | 11/1991 | Pryor et al. |
| 5,064,435 A | 11/1991 | Porter |
| 5,071,407 A | 12/1991 | Termin et al. |
| 5,073,694 A | 12/1991 | Tessier et al. |
| 5,078,720 A | 1/1992 | Burton et al. |
| 5,078,726 A | 1/1992 | Kreamer |
| 5,078,736 A | 1/1992 | Behl |
| 5,084,065 A | 1/1992 | Weldon et al. |
| 5,089,005 A | 2/1992 | Harada |
| 5,089,006 A | 2/1992 | Stiles |
| 5,092,877 A | 3/1992 | Pinchuk |
| 5,100,429 A | 3/1992 | Sinofsky et al. |
| 5,102,417 A | 4/1992 | Palmaz |
| 5,104,404 A | 4/1992 | Wolff |
| 5,108,416 A | 4/1992 | Ryan et al. |
| 5,108,417 A | 4/1992 | Sawyer |
| 5,116,318 A | 5/1992 | Hillstead |
| 5,116,360 A | 5/1992 | Pinchuk et al. |
| 5,116,365 A | 5/1992 | Hillstead |
| 5,122,154 A | 6/1992 | Rhodes |
| 5,123,917 A | 6/1992 | Lee |
| 5,133,732 A | 7/1992 | Wiktor |
| 5,135,536 A | 8/1992 | Hillstead |
| 5,158,548 A | 10/1992 | Lau et al. |
| 5,161,547 A | 11/1992 | Tower |
| 5,163,951 A | 11/1992 | Pinchuk et al. |
| 5,163,952 A | 11/1992 | Froix |
| 5,163,958 A | 11/1992 | Pinchuk |
| 5,171,262 A | 12/1992 | MacGregor |
| 5,180,368 A | 1/1993 | Garrison |
| 5,183,085 A | 2/1993 | Timmermans |
| 5,192,297 A | 3/1993 | Hull |
| 5,192,307 A | 3/1993 | Wall |
| 5,192,311 A | 3/1993 | King et al. |
| 5,195,984 A | 3/1993 | Schatz |
| 5,197,978 A | 3/1993 | Hess |
| 5,217,482 A | 6/1993 | Keith |
| 5,222,971 A | 6/1993 | Willard et al. |
| 5,226,913 A | 7/1993 | Pinchuk |
| 5,234,456 A | 8/1993 | Silvestrini |
| 5,242,394 A | 9/1993 | Tremulis |
| 5,242,399 A | 9/1993 | Lau et al. |
| 5,242,452 A | 9/1993 | Inoue |
| 5,282,823 A | 2/1994 | Schwartz et al. |
| 5,282,824 A | 2/1994 | Gianturco |
| 5,290,295 A | 3/1994 | Querals et al. |
| 5,290,305 A | 3/1994 | Inoue |
| 5,292,331 A | 3/1994 | Boneau |
| 5,304,200 A | 4/1994 | Spaulding |
| 5,314,444 A | 5/1994 | Gianturco |
| 5,314,472 A | 5/1994 | Fontaine |
| 5,330,500 A | 7/1994 | Song |
| 5,344,426 A | 9/1994 | Lau et al. |
| 5,354,308 A | 10/1994 | Simon et al. |
| 5,356,433 A | 10/1994 | Rowland et al. |
| 5,360,401 A | 11/1994 | Turnland et al. |
| 5,368,566 A | 11/1994 | Crocker |
| 5,372,600 A | 12/1994 | Beyar et al. |
| 5,378,239 A | 1/1995 | Termin et al. |
| 5,383,892 A | 1/1995 | Cardon et al. |
| 5,405,378 A | 4/1995 | Strecker |
| 5,421,955 A | 6/1995 | Lau et al. |
| 5,423,745 A | 6/1995 | Todd et al. |
| 5,423,885 A | 6/1995 | Williams |
| 5,445,646 A | 8/1995 | Euteneuer et al. |
| 5,449,373 A | 9/1995 | Pinchasik et al. |
| 5,456,694 A | 10/1995 | Marin et al. |
| 5,458,615 A | 10/1995 | Klemm et al. |
| 5,476,476 A | 12/1995 | Hillstead |
| 5,484,449 A | 1/1996 | Amundson et al. |
| 5,507,768 A | 4/1996 | Lau et al. |
| 5,514,154 A | 5/1996 | Lau et al. |
| 5,545,132 A | 8/1996 | Fagan et al. |
| 5,571,135 A | 11/1996 | Fraser et al. |
| 5,575,816 A * | 11/1996 | Rudnick et al. ........... 623/1.15 |
| 5,575,818 A * | 11/1996 | Pinchuk ................ 623/1.15 |
| 5,603,721 A | 2/1997 | Lau et al. |
| 5,626,604 A | 5/1997 | Cottone, Jr. |
| 5,630,829 A * | 5/1997 | Lauterjung ............ 623/1.15 |
| 5,653,690 A | 8/1997 | Booth et al. |
| 5,653,691 A | 8/1997 | Rupp et al. |
| 5,653,727 A * | 8/1997 | Wiktor ................ 623/1.15 |
| 5,716,396 A | 2/1998 | Williams, Jr. |
| 5,720,726 A | 2/1998 | Marcadis et al. |
| 5,733,303 A | 3/1998 | Israel et al. |
| 5,733,325 A | 3/1998 | Robinson et al. |
| 5,735,893 A | 4/1998 | Lau et al. |
| 5,782,855 A | 7/1998 | Lau et al. |
| 5,800,521 A | 9/1998 | Orth |
| 5,810,871 A | 9/1998 | Tuckey et al. |
| 5,817,152 A | 10/1998 | Birdsall et al. |
| 5,830,217 A | 11/1998 | Ryan |
| 5,836,965 A | 11/1998 | Jendersee et al. |
| 5,893,852 A | 4/1999 | Morales |
| 5,902,332 A | 5/1999 | Schatz |
| 5,913,895 A | 6/1999 | Burpee et al. |
| 5,984,964 A | 11/1999 | Roberts et al. |
| 5,997,468 A | 12/1999 | Wolff et al. |
| 6,030,413 A | 2/2000 | Lazarus |
| 6,066,168 A | 5/2000 | Lau et al. |

| | | | |
|---|---|---|---|
| 6,086,604 | A | 7/2000 | Fischell et al. |
| 6,146,358 | A | 11/2000 | Rowe |
| 6,179,868 | B1 | 1/2001 | Burpee et al. |
| 6,183,506 | B1 | 2/2001 | Penn et al. |
| 6,190,403 | B1 | 2/2001 | Fischell et al. |
| 6,217,608 | B1 | 4/2001 | Penn et al. |
| 2002/0058988 | A1 | 5/2002 | Fischell et al. |
| 2002/0058989 | A1 | 5/2002 | Chen et al. |

FOREIGN PATENT DOCUMENTS

| | | |
|---|---|---|
| EP | 0 372 789 A3 | 6/1990 |
| EP | 0 380 668 A1 | 8/1990 |
| EP | 0 407 951 A3 | 1/1991 |
| EP | 9 408 245 A1 | 1/1991 |
| EP | 0 421 729 A2 | 4/1991 |
| EP | 0 423 916 A1 | 4/1991 |
| EP | 0 428 479 A1 | 5/1991 |
| EP | 0 517 075 B1 | 12/1992 |
| EP | 0 540 290 A2 | 5/1993 |
| EP | 0 807 424 A2 | 11/1997 |
| GB | 2 070 490 A | 9/1981 |
| GB | 2 135 585 A | 11/1983 |
| JP | 62-213762 | 9/1987 |
| JP | 62-235496 A | 10/1987 |
| JP | 63-214264 | 9/1988 |
| JP | 62-246178 | 10/1988 |
| JP | 01083685 A | 3/1989 |
| JP | 2-174859 | 7/1990 |
| JP | 2-255157 | 10/1990 |
| JP | 03009745 A | 1/1991 |
| JP | 03009746 A | 1/1991 |
| JP | 4-25755 | 2/1992 |
| WO | WO 89/01798 | 3/1989 |
| WO | WO 89/08433 | 9/1989 |
| WO | WO 91/07139 | 5/1991 |
| WO | WO 92/06734 | 4/1992 |
| WO | WO 92/09246 | 6/1992 |

OTHER PUBLICATIONS

Dotter, Charles T., *Transluminal Expandable Nitinol Coil Stent Grafting: Preliminary Report, Radiology Journal*, pp. 259–260, Apr. 1983.

Cragg et al., *Non–Surgical Placement of Arterial Endoprostheses: A New Technique Using Nitinol Wire, Radiology Journal*, pp. 261–263, Apr. 1983.

Maass, et al., *Radiological Follow–Up of Transluminally Inserted Vascular Endoprostheses: An Experimental Study Using Expanding Spirals, Radiology Journal*, pp. 659–663, 1984.

C.R. Bard, *PE Plus Peripheral Balloon Dilation Catheter*, C.R. Bard, Inc., Aug. 1985.

Wright, et al., *Percutaneous Endovascular Stents: An Experimental Evaluation, Radiology Journal*, pp. 69–72, 1985.

Palmaz et al., *Expandable Intraluminal Graft: A Preliminary Study, Radiology Journal*, pp. 73–77, 1985.

Dupral et al., *Flexible Balloon–Expanded Stent for Small Vessels, Radiology Journal*, pp. 276–278 (1987).

Yoshioka et al., *Self–Expanding Endovascular Graft: An Experimental Study in Dogs, American Journal of Roentgeriology*, pp. 673–676, vol. 151, Oct. 1988.

Rosch, Jr., M.D. et al., *Transjugular Intrahepatic Portacaval Shunt: An Experimental Work, The American Journal of Surgery*, pp. 588–592, vol. 121, May 1971.

70th *Scientific Assembly and Annual Meeting: Scientific Program, Radiology*, Washington, D.C., Nov. 25–30, 1984, special Edition, vol. 153(P).

Charnsangavej, D., M.D. et al., *Endovascular Stent for Use in Aortic Dissection: An In Vitro Experiment, Radiology*, pp. 323–324, vol. 157, No. 2, Nov. 1985.

72nd *Scientific Assembly and Annual Meeting: RSNA Scientific Program, Radiology*, Chicago: Nov. 30–Dec. 5, 1986, Special Edition, vol. 161(P).

Wallace, Michael J., et al., *Tracheobronchia Tree: Expandable Metallic Stents Used in Experimental and Clinical Applications (Work in Progress), Radiology*, pp. 309–312, vol. 158, Feb. 1986.

*Program: Day 2 (Nov. 18) The Radiological Society of North America, Radiology*, Chicago: Nov. 30–Dec. 5, 1986, Special Edition, vol. 161(P).

Charnsangavej, Chusilp, M.D., et al., *Stenosis of the Vena Cava: Preliminary Assessment of Treatment with Expandable Metallic Stents, Radiology*, pp. 295–298, vol. 161, Nov. 1986.

Rosch, Josef, M.D., et al., *Experimental Intrahepatic Portacaval Anastomosis: Use of Expandable Gianturco Stents, Radiology*, pp. 481–485, vol. 162, Feb. 1987.

Rosch, Josef, M.D., et al., *Gianturco Expandable Stents in Experimental and Clinical Use*, paper presented at The Twelfth Annual Course on "Diagnostic Angiography and Interventional Radiology" Mar. 23–26, 1987 (Pittsburgh, Pennsylvania).

Finci, Leo, M.D., et al., *Percutaneous Transluminal Coronary Angioplasty of a Bifurcation Narrowing Using the Kissing Wire Monorail Balloon Technique, The American Journal of Cardiology*, pp. 375–376, vol. 60, Aug. 1987.

Lawrence, David D., Jr., M.D., et al., *Percutaneous Endovascular Graft: Experimental Evaluation, Radiology*, pp. 357–360, vol. 163, May 1987.

Rosch, Josef, M.D., et al., *Gianturco Expandable Wire Stents in the Treatment of Superior Vena Cava Syndrome Recurring after Maximum–Tolerance Radiation, Cancer*, pp. 1243–1246, vol. 60, Sep. 1987.

Bonzel, T., et al., *The Sliding Rail System (Monorail): Descriptionof a New Technique for Intravascular Instrumentation and Its Application to Coronary Angioplasty, Kardiologie*, Supplement 6, pp. 119–122, 1987.

Rosch, Josef, M.D., et al., *Modified Gianturco Expandable Wire Stents in Experimental and Clinical Use, Annales de Radiologie*, pp. 100–103, vol. 31, No. 2, 1988.

Yoshioka et al,, *Development and Clinical Application of Biliary Endoprosthesis Using Expandable Metallic Stents, Japan Radiological Society*, 1988, vol. 48, No. 9, pp. 1183–1185 (with translaton).

Mirich, et al., *Percutaneously Placed Endovascular Grafts for Aoertic Aneurysms: Feasibility Study, Radiology*, 1989, part 2, pp. 1033–1037.

Furui, Shigeru, M.D., et al., *Hepatic Inferior Vena Cava Obstruction: Treatment of Two Types with Gianturco Expandable Metallic Stents, Radiology*, pp. 665–670, Sep. 1990.

Kattenbach, M., Prof. Dr., Abstracts, *Zeitschrift fur Kardiologie*, Apr. 3, 1991 (German only).

van der Geissen, Willem J., et al., *Coronary Stenting with a New, Radiopaque Balloon–Expandable Endoprosthesis in Pigs, Circulation*, vol. 83, No. 5, pp. 93–149, May 1991.

Strupp, G., et al., *Clinical and Angiographic Short and Medium Term Results after Coronary Stenting, Zietschrift fur Kardiologie*, Sep. 9, 1992 (German with English language summary).

Harrington, J.D., et al., *The Palmaz–Schatz Stent, Handbook of Cardiovascular Internventions/Vascular Interventions*, pp. 563–572 (undated).

\* cited by examiner

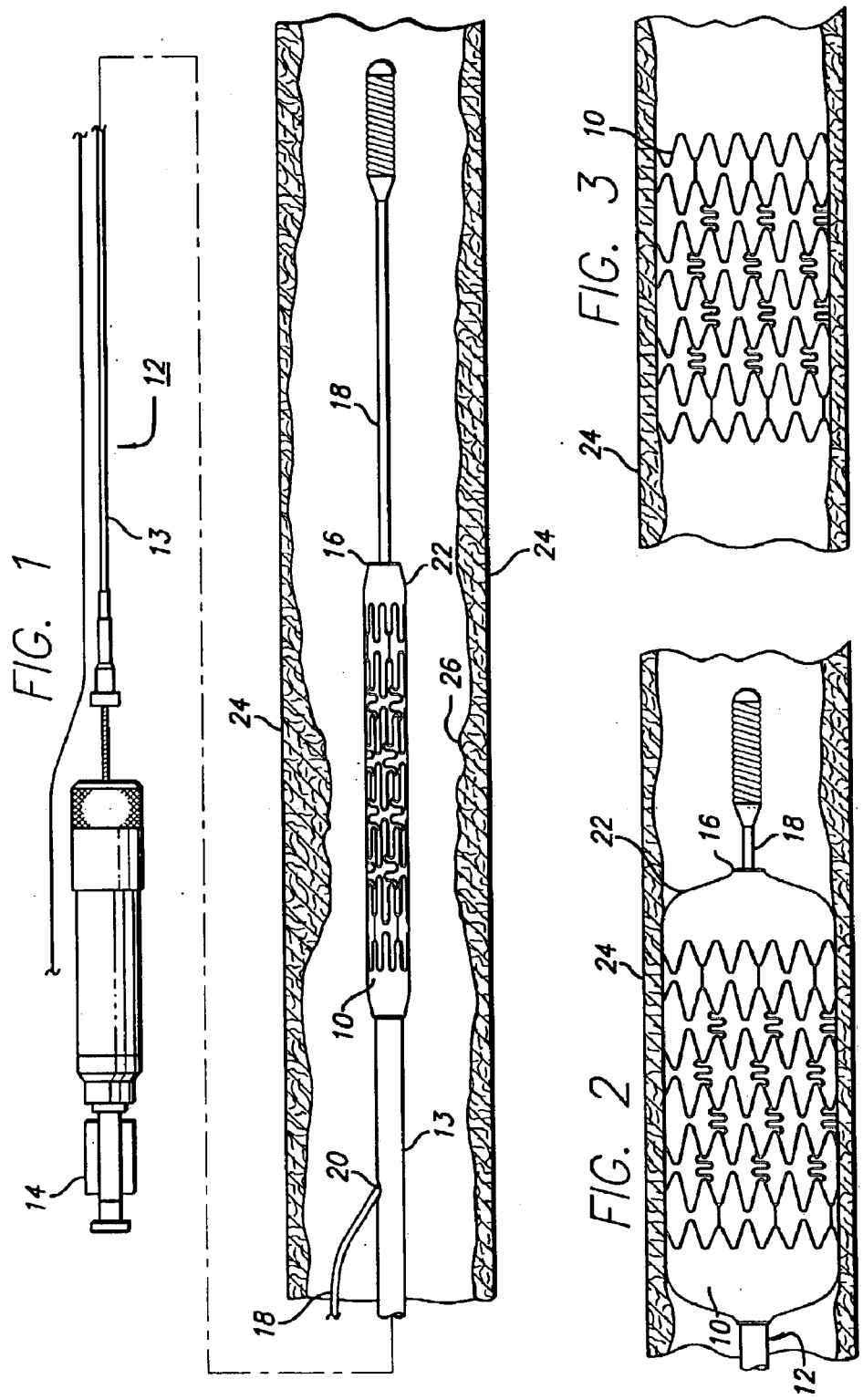

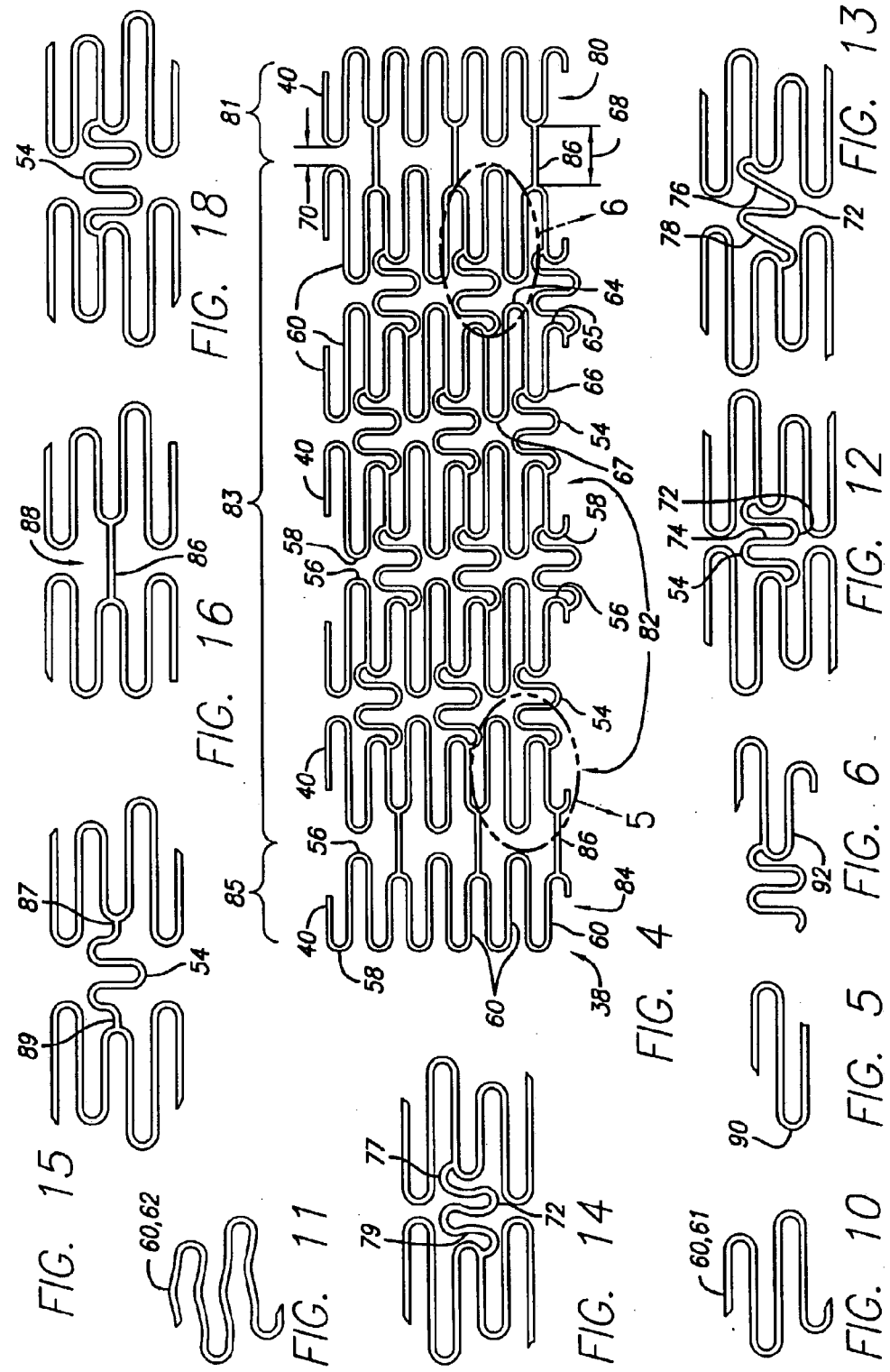

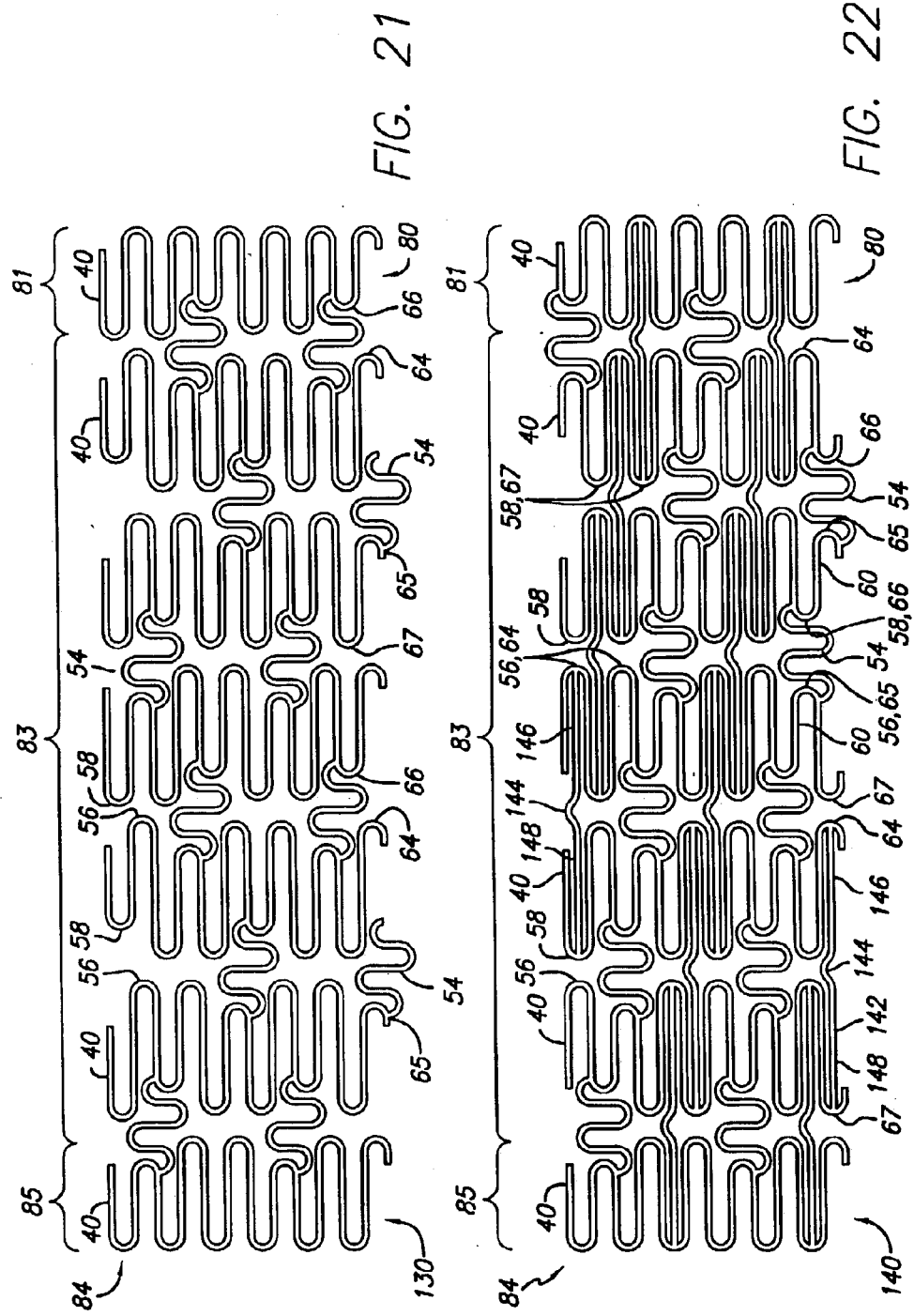

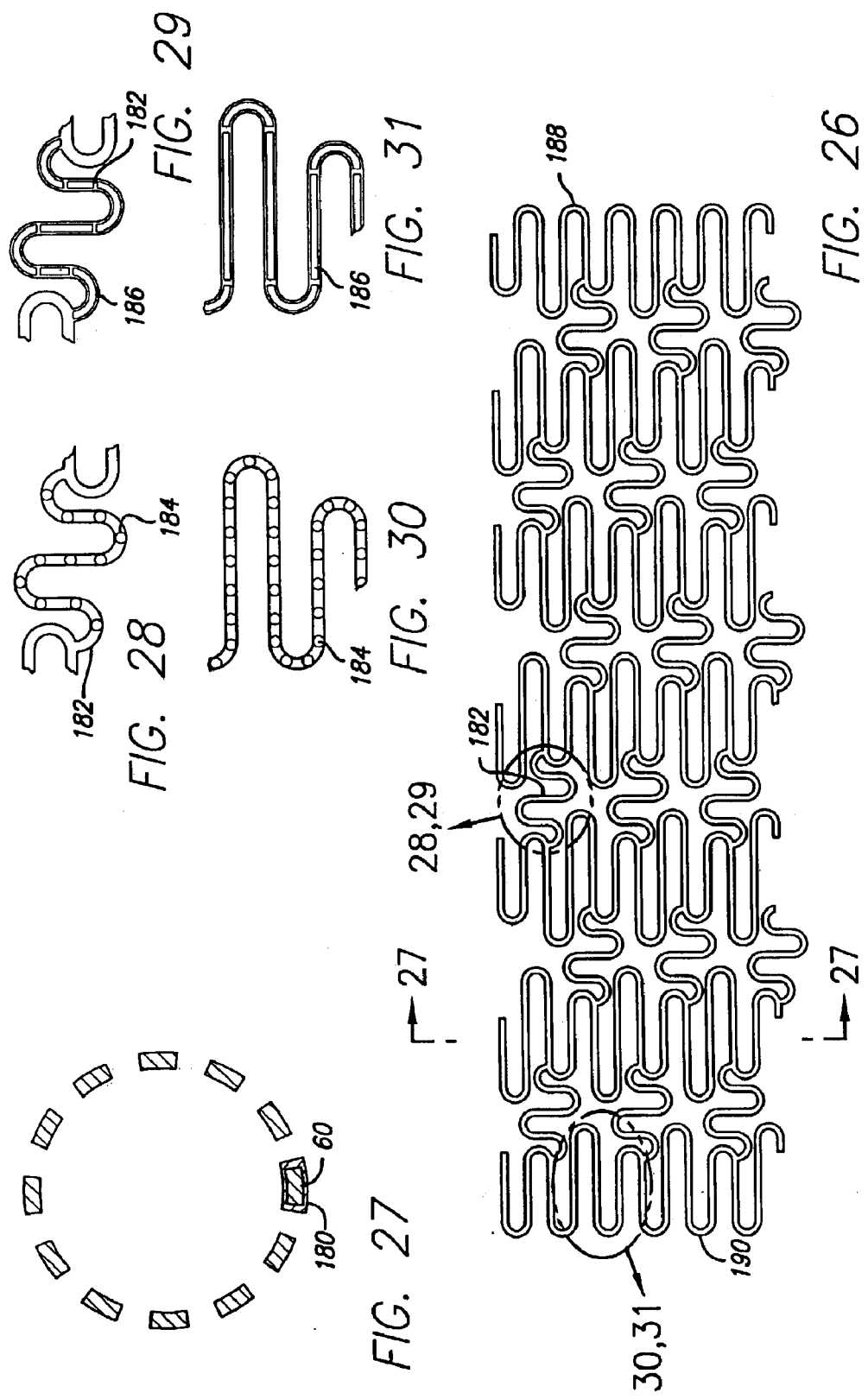

US 6,896,697 B1

INTRAVASCULAR STENT

BACKGROUND OF THE INVENTION

This invention relates to vascular repair devices, and in particular to intravascular stents, which are adapted to be implanted into a patient's body lumen, such as a blood vessel or coronary artery, to maintain the patency thereof. Stents are particularly useful in the treatment of atherosclerotic stenosis in arteries and blood vessels.

Stents are particularly useful in the treatment and repair of blood vessels after a stenosis has been compressed by percutaneous transluminal coronary angioplasty (PTCA), percutaneous transluminal angioplasty (PTA), or removed by atherectomy or other means, to help improve the results of the procedure and reduce the possibility of restenosis. Stents also can be used to provide primary compression to a stenosis in cases in which no initial PTCA or PTA procedure is performed. While stents are most often used in the procedures mentioned above, they also can be implanted on another body lumen such as the carotid arteries, peripheral vessels, urethra, esophagus and bile duct.

In typical PTCA procedures, a guiding catheter or sheath is percutaneously introduced into the cardiovascular system of a patient through the femoral arteries and advanced through the vasculature until the distal end of the guiding catheter is in the aorta. A guidewire and a dilatation catheter having a balloon on the distal end are introduced through the guiding catheter with the guidewire sliding within the dilatation catheter. The guidewire is first advanced out of the guiding catheter into the patient's vasculature and is directed across the arterial lesion. The dilatation catheter is subsequently advanced over the previously advanced guidewire until the dilatation balloon is properly positioned across the arterial lesion. Once in position across the lesion, the expandable balloon is inflated to a predetermined size with a radiopaque liquid at relatively high pressure to displace the atherosclerotic plaque of the lesion against the inside of the artery wall and thereby dilate the lumen of the artery. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

In angioplasty procedures of the kind referenced above, abrupt reclosure may occur or restenosis of the artery may develop over time, which may require another angioplasty procedure, a surgical bypass operation, or some other method of repairing or strengthening the area. To reduce the likelihood of the occurrence of abrupt reclosure and to strengthen the area, a physician can implant an intravascular prosthesis for maintaining vascular patency, commonly known as a stent, inside the artery across the lesion. Stents are generally cylindrically shaped devices which function to hold open and sometimes expand a segment of a blood vessel or other arterial lumen, such as a coronary artery. Stents are usually delivered in a compressed condition to the target location and then are deployed into an expanded condition to support the vessel and help maintain it in an open position. The stent is usually mounted onto a delivery catheter and transported in its delivery diameter through the patient's vasculature. The stent is expandable upon application of a controlled force, often through the inflation of the balloon portion of the delivery catheter, which expands the compressed stent to a larger diameter to be left in place within the artery at the target location. The stent also may be of the self-expanding type formed from, for example, shape memory metals or super-elastic nickel-titanum (NiTi) alloys, which will automatically expand from a compressed state when the stent is advanced out of the distal end of the delivery catheter into the body lumen.

The above described, non-surgical interventional procedures, when successful, avoid the necessity for major surgical operations. Many prior art stents balance between stiffness and stability to maintain the patency of a body lumen when the stent is implanted therein and flexibility along its longitudinal axis to facilitate maneuverability through tortuous body lumens. Typically, stents having high stiffness for maintaining patency of the body lumen have less flexibility than is desired for maneuvering the stent through tortuous vasculature.

What has been needed is a stent having high flexibility to facilitate maneuverability through tortuous vasculature and which maintains stiffness and stability for maintaining patency of body lumens. The present invention satisfies these needs.

SUMMARY OF THE INVENTION

The present invention is directed to an intravascular stent which is flexible along its longitudinal axis to facilitate delivery through tortuous body lumens, but which is stiff and stable enough radially in its expanded condition to maintain the patency of a body lumen such as an artery when the stent is implanted therein.

The stent assembly embodying features of the invention can be readily delivered to the desired body lumen, such as a coronary artery (may also be used in peripheral vessels, bile ducts, etc.), by mounting the stent assembly onto an expandable member of a delivery catheter, for example a balloon, and advancing the catheter and stent assembly through the body lumen to the target site. Generally, the stent is crimped onto the balloon portion of the catheter so that the stent assembly does not move longitudinally relative to the balloon portion of the catheter during delivery through the arteries, and during expansion of the stent at the target site. The stent is relatively flexible along its longitudinal axis to facilitate delivery through tortuous body lumens, yet is stiff and stable enough radially in an expanded condition to maintain the patency of a body lumen, such as an artery, when implanted therein.

In one embodiment, the stent includes a plurality of cylindrical rings and a plurality of links coupling adjacent cylindrical rings. The plurality of cylindrical rings include a proximal ring, at least one central ring and a distal ring. Each cylindrical ring includes a strut pattern having a proximal end and a distal end while the proximal and distal ends define a ring length. The cylindrical rings are coaxially aligned along a common longitudinal axis forming the stent and radially expandable with a first delivery diameter and a second implanted diameter. The strut pattern of each of the cylindrical rings includes an undulating pattern of U-shaped portions with the curved portions of the U-shapes being positioned at the proximal and distal ends of the struts. The U-shapes at the proximal end of the cylindrical rings are referred to as peaks while the U-shapes at the distal end of the cylindrical rings are referred to as valleys. The peaks and valleys have struts extending therebetween. Adjacent valleys of the proximal ring alternate between a first, proximal position along the longitudinal axis of the stent and a second, distal position along the longitudinal axis of the stent. Adjacent peaks of the at least one central ring alternate between a first, proximal position and a second, distal position. Adjacent valleys of the at least one central ring also alternate between a first, proximal position and a second, distal position. Further, adjacent peaks of the distal ring alternate between a first, proximal position and a second, distal position. The peaks of each cylindrical ring are circumferentially aligned with the valleys of the adjacent cylindrical ring. The links couple alternating peaks on one cylindrical ring to circumferentially aligned valleys on the proximally adjacent cylindrical ring.

In one aspect of the invention, the peaks positioned at the second, distal position are circumferentially aligned with the valleys positioned at the first, proximal position of the proximally adjacent cylindrical ring with the links coupling the adjacent rings therebetween. Varying embodiments include the distal and proximal ends of the links being coupled to the apices of the peaks and valleys, respectively, or at a distance from the apices of the peaks and valleys. Embodiments having the distal and proximal ends of the links coupled at a distance from the apices of the peaks and valleys include the ends being coupled to the same side of the respective apices of the peak and valley or to opposite sides of the respective apices of the peak and valley.

In other embodiments of the invention, adjacent peaks of the proximal ring alternate between a first, proximal position along the longitudinal axis of the stent and a second, distal position. Similarly, adjacent valleys of the distal ring alternate between a first, proximal position and a second, distal position. However, adjacent peaks of the proximal ring may also be longitudinally aligned along the longitudinal axis of the stent (i.e., at the same longitudinal position along the longitudinal axis of the stent), and adjacent valleys of the distal ring may be longitudinally aligned. The ring length of each of the central rings may be greater than the ring lengths of the proximal and distal rings. In one aspect of the invention, the links positioned between central rings include an undulating configuration, while the links positioned between the proximal ring and the distally adjacent central ring and the links positioned between the distal ring and the proximally adjacent central ring may include a straight configuration. In another aspect of the invention, all of the links include an undulating configuration having a plurality of curved portions with struts extending therebetween. The struts of the links may include a straight configuration with the struts positioned perpendicular to the longitudinal axis of the stent, a straight configuration with the struts positioned at an angle to the longitudinal axis of the stent, or a curved configuration. The struts of the cylindrical rings may include either a straight configuration or a curved configuration. At least a portion of the stent may be coated with a drug. The stent may also include flexing portions and stable portions. The flexing portions may include a nominal thickness and a nominal width, while the stable portions may include a greater-than-nominal thickness or a greater-than-nominal width.

In another embodiment of the invention, the peaks of each cylindrical ring are circumferentially aligned with the peaks of the adjacent cylindrical ring. The links couple alternating peaks on one cylindrical ring to circumferentially adjacent valleys on the proximally adjacent cylindrical ring. In one aspect of the invention, the peaks positioned at the second, distal position are circumferentially aligned with the peaks positioned at the first, proximal position of the proximally adjacent cylindrical ring and the links couple the peaks positioned at the second, distal position on one cylindrical ring to the circumferentially adjacent valleys positioned at the first, proximal position on the proximally adjacent cylindrical ring.

In a further embodiment of the invention, valleys of the proximal ring alternate between a single valley at a first, proximal position along the longitudinal axis of the stent and a pair of adjacent valleys at a second, distal position. Peaks of the at least one central ring alternate between a pair of adjacent peaks at a first, proximal position and a single peak at a second, distal position. Valleys of the at least one central ring alternate between a single valley at a first, proximal position and a pair of adjacent valleys at a second, distal position along the longitudinal axis of the stent. Each of the peaks at the second, distal position of the at least one central ring is positioned between a pair of adjacent valleys at the second, distal position and each of the valleys at the first, proximal position is positioned between a pair of adjacent peaks at the first, proximal position. Peaks of the distal ring alternate between a pair of adjacent peaks at a first, proximal position along the longitudinal axis of the stent and a single peak at a second, distal position along the longitudinal axis of the stent. The peaks of each cylindrical ring are circumferentially aligned with the valleys of the adjacent cylindrical ring. The links couple peaks on one cylindrical ring to circumferentially aligned valleys on the proximally adjacent cylindrical ring.

In a another embodiment of the invention, the peaks positioned at the second, distal position are circumferentially aligned with the valleys positioned at the first, proximal position of the proximally adjacent cylindrical ring with the links coupling the adjacent rings therebetween. Peaks of the proximal ring may alternate between a pair of adjacent peaks at a first, proximal position and a single peak at a second, distal position. In this configuration, each single peak at the second, distal position is positioned between a pair of adjacent valleys at the second, distal position and each single valley at the first, proximal position is positioned between a pair of adjacent peaks at the first, proximal position. Similarly, valleys of the distal ring may alternate between a single valley at a first, proximal position and a pair of adjacent valleys at a second, distal position. Each single valley at the first, proximal position is positioned between a pair of adjacent peaks at the first, proximal position and each single peak at the second, distal position is positioned between a pair of adjacent valleys at the second, distal position.

Another embodiment of the invention also incorporates peaks alternating between a pair of adjacent peaks at a first, proximal position and a single peak at a second, distal position and valleys alternating between a single valley at a first, proximal position and a pair of valleys at a second, distal position. In this embodiment, however, the peaks of each cylindrical ring are circumferentially aligned with the peaks of the adjacent cylindrical ring. The links couple peaks on one cylindrical ring to circumferentially adjacent valleys on the proximally adjacent cylindrical ring. In one aspect of the invention, the peaks positioned at the second, distal position are circumferentially adjacent to the valleys positioned at the first, proximal position of the proximally adjacent cylindrical ring. The links couple the peaks positioned at the second, distal position on one cylindrical ring to the circumferentially adjacent valleys positioned at the first, proximal position on the proximally adjacent cylindrical ring.

A further embodiment of the invention also incorporates peaks alternating between a pair of adjacent peaks at a first, proximal position and a single peak at a second, distal position and valleys alternating between a single valley at a first, proximal position and a pair of valleys at a second, distal position. In this embodiment, however, the at least one central ring includes a peak at the first, proximal position positioned between each pair of adjacent valleys at the second, distal position and a valley at the second, distal position positioned between each pair of adjacent peaks at the first, proximal position. Each peak at the distal position is circumferentially adjacent to a valley at the proximal position. The peaks of each cylindrical ring are circumferentially aligned with the valleys of the adjacent cylindrical ring. The stent includes a plurality of undulating links and a plurality of links having straight portions and at least one curved portion coupling a plurality of adjacent cylindrical rings. The undulating links couple a plurality of adjacent cylindrical rings between peaks on one cylindrical ring to circumferentially aligned valleys on the proximally adjacent cylindrical rings. The links having the straight portions and at least one curved portion, however, couple a plurality of adjacent cylindrical rings between valleys positioned between circumferentially adjacent pairs of peaks at the proximal position on the distally adjacent cylindrical rings to the circumferentially aligned peaks on the proximally adjacent rings.

In another embodiment of the invention, the peaks that are positioned at the second, distal position of one ring are circumferentially aligned with the valleys that are positioned at the first, proximal position of the proximally adjacent cylindrical ring. The undulating links couple a plurality of adjacent cylindrical rings between the peaks positioned at the second, distal position on one cylindrical ring to the circumferentially aligned valleys positioned at the first, proximal position on the proximally adjacent cylindrical ring. The links which have the straight portions and at least one curved portion couple a plurality of adjacent cylindrical rings between valleys which are positioned between circumferentially adjacent pairs of peaks at the proximal position on one ring to the circumferentially aligned peaks which are positioned between a circumferentially aligned pair of valleys at the distal position on the proximally adjacent cylindrical ring.

In an additional embodiment of the invention, a stent includes a plurality of cylindrical rings, a plurality of undulating links that couple a plurality of cylindrical rings, and a plurality of links having straight portions and at least one curved portion that couple a plurality of adjacent cylindrical rings. The strut pattern of the cylindrical rings may be configured such that when the stent is in the second implanted diameter, the circumferential distance between adjacent peaks on the cylindrical rings are variable about the circumference of the cylindrical rings. Similarly, the circumferential distance between adjacent valleys on the cylindrical rings may also be variable about the circumference of the cylindrical rings. Due to the variability of the circumferential distance between adjacent peaks and between adjacent valleys, between adjacent cylindrical rings at least one peak on the distally adjacent ring is circumferentially aligned with a valley on the proximally adjacent cylindrical ring. At least one other peak on the distally adjacent ring is circumferentially aligned with a peak on the proximally adjacent cylindrical ring. At least one valley on the distally adjacent ring is circumferentially aligned with a valley on the proximally adjacent cylindrical ring, and at least one other valley on the distally adjacent ring is circumferentially aligned with a peak on the proximally adjacent cylindrical ring. The undulating links couple a plurality of pairs of adjacent cylindrical rings between at least one peak on the distally adjacent cylindrical ring and the circumferentially aligned valley on the proximally adjacent cylindrical ring. The links having the straight portions and at least one curved portion couple at least one pair of adjacent cylindrical rings between at least one peak on the distally adjacent cylindrical ring and the circumferentially aligned peak on the proximally adjacent cylindrical ring, between at least one valley on the distally adjacent cylindrical ring and the circumferentially aligned valley on the proximally adjacent cylindrical ring, and between at least one valley on the distally adjacent cylindrical ring and the circumferentially aligned peak on the proximally adjacent cylindrical ring.

In another embodiment of the invention, the curved portions of at least one of the links that has straight portions and at least one curved portion are positioned between the adjacent cylindrical rings to which the link is coupled. In another aspect of the invention, the curved portions of at least one of the links having straight portions and at least one curved portion are positioned between the struts of at least one of the adjacent cylindrical rings to which the link is coupled.

Each of the embodiments of the invention can be readily delivered to the desired luminal location by mounting them on an expandable member of a delivery catheter, for example a balloon, and passing the catheter-stent assembly through the body lumen to the implantation site. A variety of means for securing the stents to the expandable member on the catheter for delivery to the desired location are available. It is presently preferred to crimp the stent onto the unexpanded balloon. Other means to secure the stent to the balloon include providing ridges or collars on the inflatable member to restrain lateral movement, using bioabsorbable temporary adhesives, or a retractable sheath to cover the stent during delivery through a body lumen.

In one embodiment, structures for the expandable cylindrical rings which form the stents of the present invention generally have circumferential undulations containing alternating peaks and valleys. The peaks and valleys are formed in generally U- and Y-shaped patterns alternately aligned along the longitudinal axis.

While the cylindrical rings and links incorporated into stents are generally not separate structures, they have been conveniently referred to as rings and links for ease of identification. Further, the cylindrical rings can be thought of as comprising a series of U- and Y-shaped structures in a repeating pattern. While the cylindrical rings are not divided up or segmented into U's and Y's, the pattern of cylindrical rings resemble such configuration. The U's and Y's promote flexibility in the stent primarily by flexing and may tip radially outwardly as the stent is delivered through a tortuous vessel.

The links which interconnect adjacent cylindrical rings can have cross-sections similar to the cross-sections of the undulating components of the cylindrical rings. The links may be formed in a unitary structure with the expandable cylindrical rings, or they may be formed independently and mechanically secured between the expandable cylindrical rings. The links may be formed substantially linearly or with a plurality of undulations.

Preferably, the number, shape and location of the links can be varied in order to develop the desired coverage area and longitudinal flexibility. These properties are important to minimize alteration of the natural physiology of the body lumen into which the stent is implanted and to maintain the compliance of the body lumen which is internally supported by the stent. Generally, the greater the longitudinal flexibility of the stents, the easier and the more safely they can be delivered to the implantation site, especially where the implantation site is on a curved section of a body lumen, such as a coronary artery or a peripheral blood vessel, and especially saphenous veins and larger vessels.

The stent may be formed from a tube by laser cutting the pattern of cylindrical rings and links in the tube, by individually forming wire rings and laser welding them together, and by laser cutting a flat metal sheet in the pattern of the cylindrical rings and links and then rolling the pattern into the shape of the tubular stent and providing a longitudinal weld to form the stent.

Other features and advantages of the present invention will become more apparent from the following detailed description of the invention, when taken in conjunction with the accompanying exemplary drawings.

BRIEF DESCRIPTION OF THE DRAWINGS

FIG. 1 is an elevational view, partially in section, of an example of a stent embodying features of the invention and which is mounted on a rapid-exchange delivery catheter and positioned within an artery.

FIG. 2 is an elevational view, partially in section, similar to that shown in FIG. 1 except that the stent is expanded within the artery, so that the stent embeds within the arterial wall.

FIG. 3 is an elevational view, partially in section, showing the expanded stent implanted within the artery after withdrawal of the rapid-exchange delivery catheter.

FIG. 4 is a plan view of a flattened stent of the invention which illustrates the pattern of the stent shown in FIGS. 1–3.

FIG. 5 is an enlarged sectional view of FIG. 4 depicting a U-shaped portion of the cylindrical ring.

FIG. 6 is an enlarged sectional view of FIG. 4 depicting a Y-shaped portion of the cylindrical ring.

FIG. 10 is an enlarged view depicting struts of the cylindrical rings in a straight configuration.

FIG. 11 is an enlarged view depicting struts of the cylindrical rings in a curved configuration.

FIG. 12 is an enlarged view depicting undulating links having straight struts extending perpendicular to the longitudinal axis of the stent and coupling to opposing sides of the apices of a peak and valley of adjacent cylindrical rings.

FIG. 13 is an enlarged view depicting undulating links having straight struts extending at an angle to the longitudinal axis of the stent and coupling to opposing sides of the apices of a peak and valley of adjacent cylindrical rings.

FIG. 14 is an enlarged view depicting undulating links having curved struts.

FIG. 15 is an enlarged view depicting undulating links coupling to the apices of a peak and valley of adjacent cylindrical rings.

FIG. 16 is an enlarged view depicting straight links coupling to the apices of a peak and valley of adjacent cylindrical rings.

FIG. 18 is an enlarged view depicting undulating links coupling to the same side of the apices of a peak and valley of adjacent cylindrical rings.

FIG. 21 is a plan view of a flattened stent of the invention which illustrates the pattern of another embodiment of the stent.

FIG. 22 is a plan view of a flattened stent of the invention which illustrates the pattern of another embodiment of the stent.

FIG. 26 is a plan view of a flattened stent having a drug coating on selected portions.

FIG. 27 is a cross-sectional view taken along lines 27—27 depicting the drug coating on a portion of the stent.

FIG. 28 is an enlarged sectional view of FIG. 26 depicting a link of the stent with micro depots distributed along the link.

FIG. 29 is an enlarged sectional view of FIG. 26 depicting a link of the stent with micro channels distributed along the link.

FIG. 30 is an enlarged sectional view of FIG. 26 depicting a cylindrical ring of the stent with micro depots distributed along the cylindrical ring.

FIG. 31 is an enlarged sectional view of FIG. 26 depicting a cylindrical ring of the stent with micro channels distributed along the cylindrical ring.

DETAILED DESCRIPTION OF THE PREFERRED EMBODIMENTS

Figure 7A:
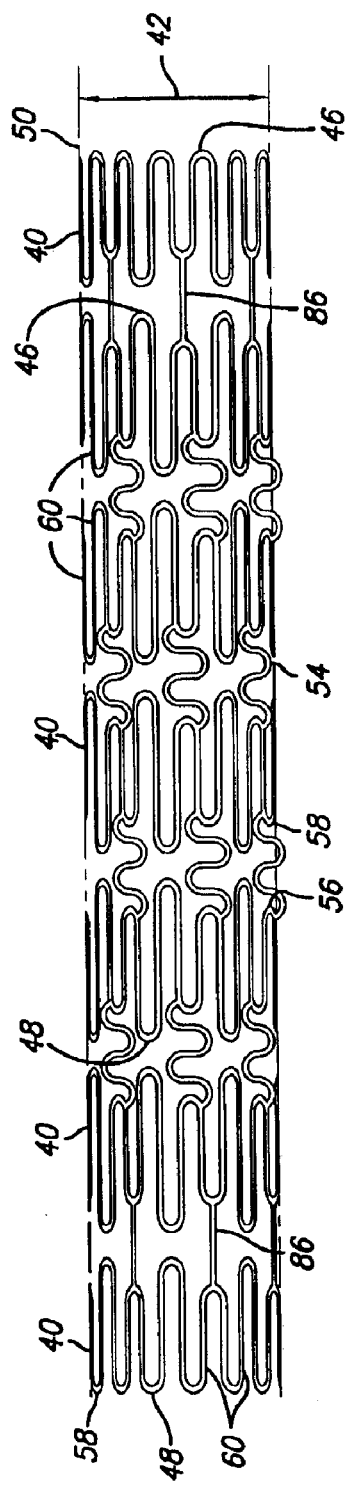
FIG. 7A is a side view of a stent embodying features of the invention in an unexpanded state.
Figure 7B:
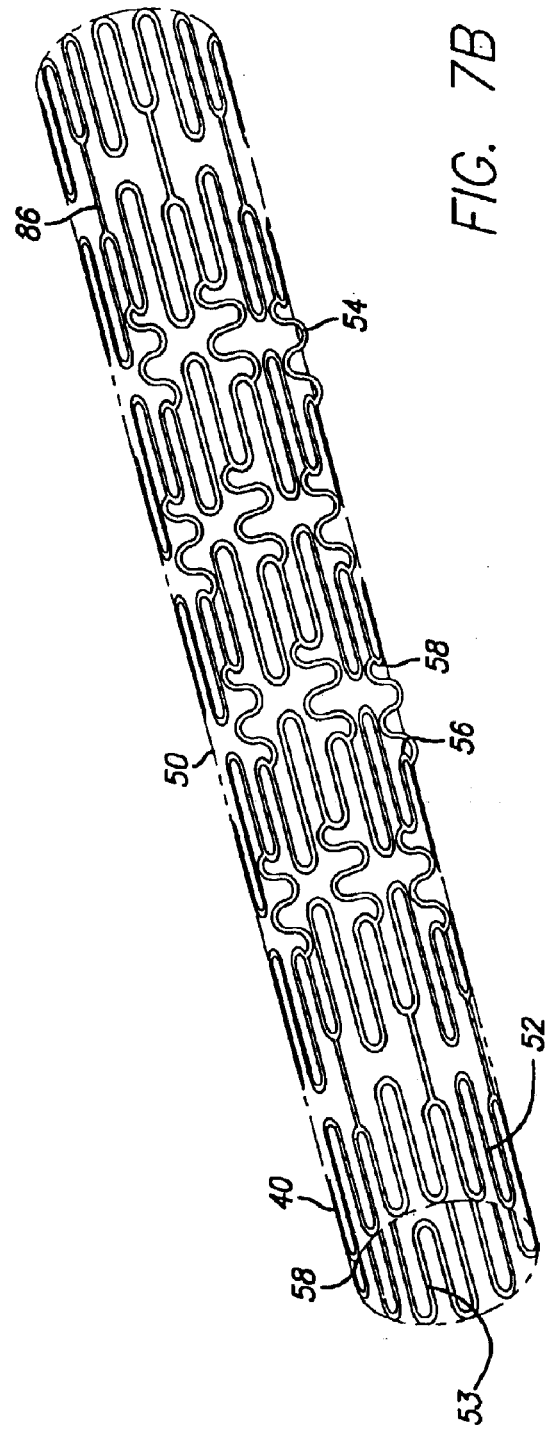
FIG. 7B is a perspective view of the stent of FIG. 7A depicting the cylindrical wall defined by each cylindrical ring.

Before describing in detail an exemplary embodiment of a stent in accordance with the present invention, it is instructive to briefly describe a typical stent implantation procedure and the vascular conditions which are typically treated with stents. Turning to the drawings, FIG. 1 depicts a balloon expandable stent 10 of the present invention mounted on a catheter assembly 12 which is used to deliver the stent and implant it in a body lumen, such as a coronary artery, peripheral artery, or other vessel or lumen within the body. The catheter assembly includes a catheter shaft 13 which has a proximal end 14 and a distal end 16. The catheter assembly is configured to advance through the patient's vascular system by advancing over a guide wire 18 by any of the well known methods of an over the wire system (not shown) or a well known rapid exchange catheter system, such as the one shown in FIG. 1.

The catheter assembly 12, as depicted in FIG. 1, is of the well known rapid exchange (RX) type which includes an RX port 20 where the guide wire 18 will exit the catheter. The distal end of the guide wire 18 exits the catheter distal end 16 so that the catheter advances along the guide wire on a section of the catheter between the RX port 20 and the catheter distal end 16. As is known in the art, the guide wire lumen which receives the guide wire is sized for receiving various diameter guide wires to suit a particular application. The stent is mounted on the expandable member 22 (e.g., balloon) and is crimped tightly thereon so that the stent and expandable member present a low profile diameter for delivery through the arteries.

As shown in FIG. 1, a partial cross-section of an artery 24 is shown with a small amount of plaque 26 that has been previously treated by an angioplasty or other repair procedure. The stent 10 of the present invention is used to repair a diseased or damaged arterial wall which may include the plaque 26 as shown in FIG. 1. The stent of the invention is configured to repair the vessel having plaque.

In a typical procedure to implant the stent 10, the guide wire 18 is advanced through the patient's vascular system by well known methods so that the distal end of the guide wire is advanced past the plaque or diseased area 26. Prior to implanting the stent, the cardiologist may wish to perform an angioplasty procedure or other procedure (i.e., atherectomy) in order to open the vessel and remodel the diseased area. Thereafter, the stent delivery catheter assembly 12 is advanced over the guide wire so that the stent is positioned in the target area. The expandable member or balloon 22 is inflated by well known means so that it expands radially outwardly and in turn expands the stent radially outwardly until the stent is apposed to the vessel wall. The expandable member is then deflated and the catheter withdrawn from the patient's vascular system. The guide wire typically is left in the lumen for post-dilatation procedures, if any, and subsequently is withdrawn from the patient's vascular system. As depicted in FIG. 2, the balloon is fully inflated with the stent expanded and pressed against the vessel wall, and in FIG. 3, the implanted stent remains in the vessel after the balloon has been deflated and the catheter assembly and guide wire have been withdrawn from the patient.

Stent 10 serves to hold open the artery after the catheter is withdrawn, as illustrated by FIG. 3. In this embodiment, due to the formation of the stent from an elongated tubular member, the undulating components of the stent are relatively flat in transverse cross-section, so that when the stent is expanded, it is pressed into the wall of the artery and as a result does not interfere with the blood flow through the artery. The stent is pressed into the wall of the artery and will eventually be covered with smooth muscle cell growth which further minimizes blood flow interference. The undulating portion of the stent provides good tacking characteristics to prevent stent movement within the artery.

In keeping with the present invention, FIGS. 4–9 depict the stent 10 in various configurations. Turning to FIG. 4, stent 10 is shown in a flattened condition so that the pattern can be clearly viewed, even though the stent is never in this form unless it is formed from a flat sheet. The stent is typically formed from a tubular member, however, it can be formed from a flat sheet such as shown in FIG. 4 and rolled into a cylindrical configuration.

With respect to the structure of the cylindrical rings and links, virtually any pattern is acceptable. Typically, the rings are in the form of a generally zig-zag pattern 38 that can easily expand radially outwardly or compress radially inwardly. Thus, as described immediately below, an example of cylindrical rings 40 and links 54 are described, however, other patterns are envisioned that would perform equally well.

Figure 8:
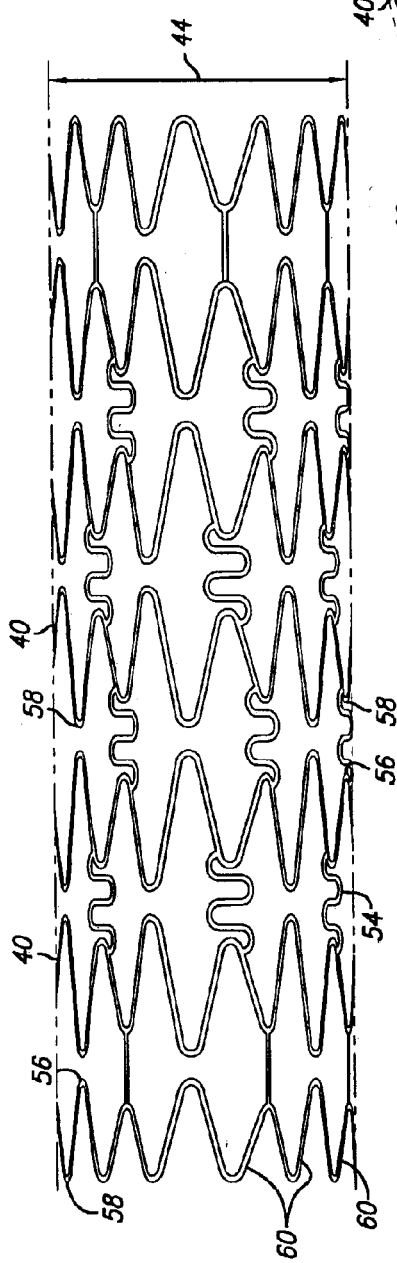
FIG. 8 is a side view of the stent of FIG. 7A in an expanded condition.
Figure 9:
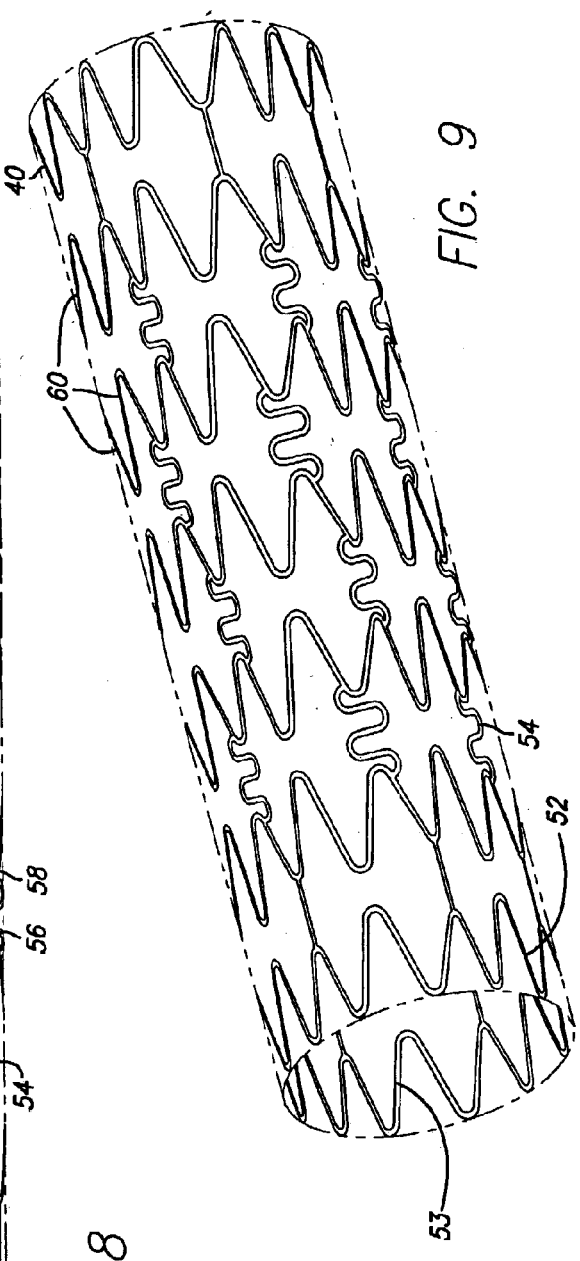
FIG. 9 is a perspective view of the stent of FIG. 7A in an expanded condition.

As shown in FIGS. 4–9, stent 10 is made up of a plurality of cylindrical rings 40 having a strut pattern. The cylindrical rings extend circumferentially around the stent when it is in a tubular form (see FIGS. 7A and 7B) and are coaxially aligned along a common longitudinal axis which forms the stent. The stent is radially expandable, thus having a first, delivery diameter 42 as shown in FIG. 7A, and a second, implanted diameter 44 (expanded diameter) as shown in FIG. 8. Each cylindrical ring 40 has a proximal end 46 and a distal end 48 with the distance between the proximal end and the distal end defining a ring length. Typically, since the stent is laser cut from a solid tube there are no discreet parts such as the described cylindrical rings. However, it is beneficial for identification and reference to various parts to refer to the cylindrical rings and the following parts of the stent.

Each cylindrical ring 40 defines a cylindrical plane 50 which is a plane defined by the proximal and distal ends 46, 48 and the circumferential extent as the cylindrical ring travels around the cylinder. Each cylindrical ring includes a cylindrical outer wall surface 52 which defines the outermost surface of the stent, and a cylindrical inner wall surface 53 which defines the innermost surface of the stent. The cylindrical plane 50 follows the cylindrical outer wall surface. In keeping with the invention, the links 54 are positioned within the cylindrical plane 50. The links couple one cylindrical ring to an adjacent cylindrical ring.

Referring to FIGS. 4–11, stent 10 can be described more particularly as having peaks 56 and valleys 58 with struts 60 positioned therebetween. Although the stent is not divided into separate elements, for ease of discussion references to peaks, valleys and struts is appropriate. The number of peaks and valleys, sometimes referred to as crowns, can vary in number for each ring depending upon the application. Thus, for example, if the stent is to be implanted in a coronary artery, a lesser number of peaks and valleys (or crowns) are required than if the stent is implanted in a peripheral artery, which has a larger diameter than a coronary artery. In one embodiment, the struts 60 of the cylindrical rings include a straight configuration 61 (FIGS. 4, 10), while in another embodiment (FIG. 11) the struts include a curved configuration 62.

As can be seen in FIG. 4, the peaks 56, are positioned at the proximal end 46 of each cylindrical ring 40, and the valleys 58 are positioned at the distal end 48 of each cylindrical ring. Further, the peaks are positioned out-of-phase, that is, the peaks of one ring 40 are circumferentially offset from the peaks of an adjacent ring 40, such that the peaks of one ring are substantially circumferentially aligned with the valleys of an adjacent ring (i.e., are aligned along lines on the circumference of the stent that are parallel to the longitudinal axis of the stent). In other words, the peaks 56 of one ring point toward the valleys 58 of a proximally adjacent ring. Positioning the peaks, valleys, and links 54 in this manner, provides a stent having uniform expansion capabilities, high radial strength and sufficient wall coverage to support the vessel. However, it may be desirable under certain circumstances to position peaks 56 so that they are in phase (FIG. 19), meaning that the peaks 56 of adjacent rings are substantially circumferentially aligned along the longitudinal axis of the stent.

With continued reference to FIG. 4, adjacent peaks 56 of each cylindrical ring 40 alternate along the longitudinal axis of the stent between a first, proximal position 64 and a second, distal position 65. Similarly, adjacent valleys 58 of each cylindrical ring 40 alternate along the longitudinal axis of the stent between a first, proximal position 66 and a second, distal position 67. In one embodiment, the peaks at the distal position of one ring are circumferentially aligned with the valleys at the proximal position of the adjacent cylindrical ring. Accordingly, the peaks 56 at the proximal position 64 of one ring 40 are circumferentially aligned with the valleys 58 at the distal position 67 of the adjacent cylindrical ring 40. In this manner, the peaks at the distal position and the valleys at the proximal position on the proximally adjacent ring are spaced at a first distance 68 which is greater than a second distance 70 between the peaks at the proximal position and the valleys at the distal position on the proximally adjacent ring.

The undulating links connect one cylindrical ring 40 to an adjacent cylindrical ring and provide overall longitudinal flexibility to the stent 10 due to their unique construction. The flexibility of undulating links derives in part from curved portions 72 with struts 74 extending therebetween. In one configuration (FIG. 12), the struts 74 are straight and extend substantially perpendicular to the longitudinal axis of the stent. With the struts being substantially perpendicular to the stent longitudinal axis, the undulating link acts like a hinge to provide flexibility. Thus, as the stent is being delivered through a tortuous vessel, such as a coronary artery, the curved portions 72 and straight struts 74 of the undulating links will permit the stent to flex in the longitudinal direction, which substantially enhances delivery of the stent to the target site. Links 76 of an alternate embodiment (FIG. 13) include straight struts 78 positioned at an angle to the longitudinal axis of the stent to form longer straight portions thereby increasing the flexibility of the links by providing longer moment arms. The longer struts positioned at the angel also increase vessel wall coverage. In a further embodiment (FIG. 14), the links 77 may include curved struts 79. The number of curved portions and struts can be increased or decreased from that shown to achieve differing flexibility constructions.

Referring again to FIG. 4, the stent 10 may include a proximal cylindrical ring 80 within a proximal region 81 of the stent, a plurality of central cylindrical rings 82 within a central region 83 of the stent and a distal cylindrical ring 84 within a distal region 85 of the stent. The ring length of the central rings may be greater than the ring length of the distal and proximal rings. The shorter ring length of the proximal and distal rings results in the proximal and distal rings being more rigid than the longer central rings. Rigid proximal and distal rings may be desirable to increase the crimp force of the proximal and distal rings onto the expandable member 22, thereby facilitating retention of the stent 10 on the expandable member during delivery of the stent to the diseased portion of the body vessel. The peaks 56 of the proximal cylindrical ring 80 may be longitudinally aligned with each other along the longitudinal axis of the stent (i.e., at the same longitudinal position along the longitudinal axis of the stent). Similarly, the valleys 58 of the distal cylindrical ring 84 may be longitudinally aligned with each other along the longitudinal axis of the stent.

In one embodiment, the links 54 positioned between adjacent pairs of central cylindrical rings 82 may include the undulating configuration to maximize flexibility of the stent throughout the central region 83. The links 86 positioned between the proximal ring 80 and the central region 83, and the links positioned between the distal ring 84 and the central region, may include a straight configuration 88 (FIGS. 4, 16) that is parallel to the longitudinal axis of the stent 10. The straight links 86 are less flexible than the undulating links 54, 76 and further increase the rigidity of the proximal and distal regions of the stent and improve the crimping force onto the expandable member 22.

Referring to FIGS. 5–6, the stent of the invention can be described as having cylindrical rings formed of an undulating pattern of U-shaped portions 90 and Y-shaped portions 92. Again, while the stent is generally laser cut from a solid tube and it typically has no discreet parts, for ease of identification the stent of the invention also can be referred to as having U- and Y-shaped portions. The U-shaped portions have no supporting structure attached thereto. The Y-shaped portions, at their base, or apex, have the link 54, 76 extending therefrom. The length of the links can vary depending upon the desired amount of separation between adjacent cylindrical rings. Preferably, the link and the Y-shaped portion are in the same cylindrical plane 50 as defined by the cylindrical outer wall surface 52 and the cylindrical inner wall surface 53.

Referring again to FIG. 4, in a present embodiment, flexibility in the stent 10 derives from the links 54, 76, 86 being coupled to alternating peaks 56 and alternating valleys 58 of the cylindrical rings 40, as opposed to links being coupled to adjacent peaks and adjacent valleys of the cylindrical rings. Coupling the links to the rings at peaks in the distal position 65 and valleys at the proximal position 66 permits adjacent cylindrical rings 40 to be positioned close together. In this manner, the distance between cylindrical rings may be minimized and the U-shaped portions including the peaks in the first, proximal position and valleys in the second distal position provide support of the vessel lumen between the links.

In one embodiment of the invention (FIG. 12), a distal end of each link 54 is coupled to a peak 56 at the distal position 65 of one ring 40 at a position a distance from the apex of the peak. A proximal end of each link is coupled to the circumferentially aligned valley 58 at the proximal position 66 of the proximally adjacent ring at a position a distance from the apex of the valley. In this manner, the links are coupled to alternating peaks and valleys. The proximal and distal ends of the link 54 may be coupled to opposing sides of the peak and valley (FIG. 12). However, in another embodiment (FIG. 18) of the link, the proximal and distal ends may be coupled to the same side of the peak and valley. In a further embodiment (FIG. 15), the distal and proximal ends of the links 54 attach to the apices of the peak 56 at the distal position 65 of one ring 40 and the valley 58 of the proximal position 66 of the proximally adjacent ring 40 respectively. In this embodiment, the links include a first or proximal arm 87 which couples to the valley of the proximal position and a second or distal arm 89 which couples to the peak of the distal position. The first and second arms extend substantially longitudinally and parallel to the longitudinal axis of the stent.

Figure 17A:
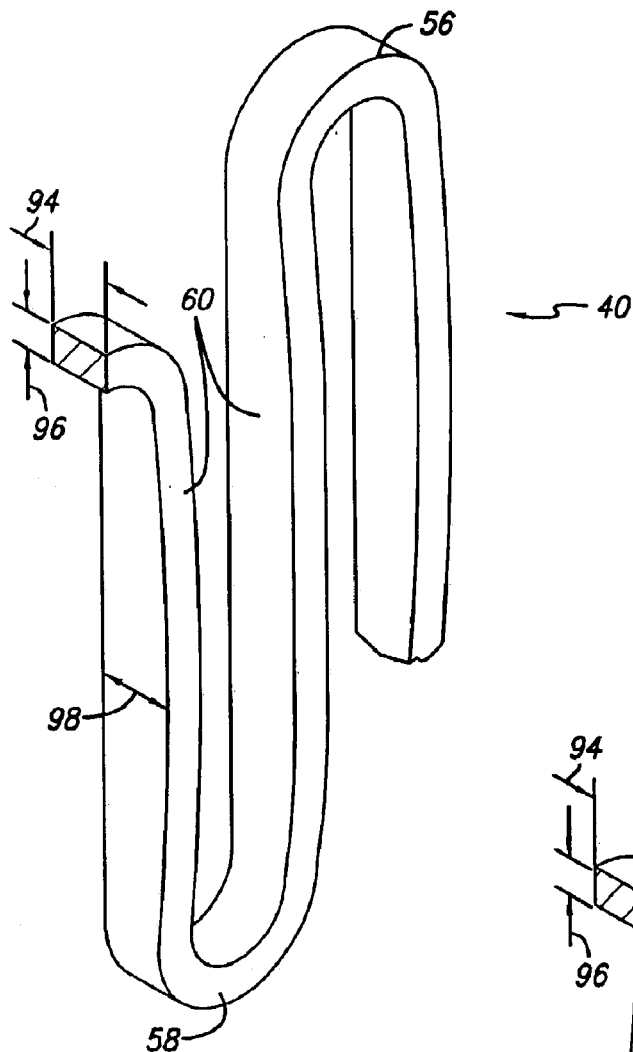
FIG. 17A is an enlarged view depicting a portion of a cylindrical ring having flexible portions and stable portions.
Figure 17B:
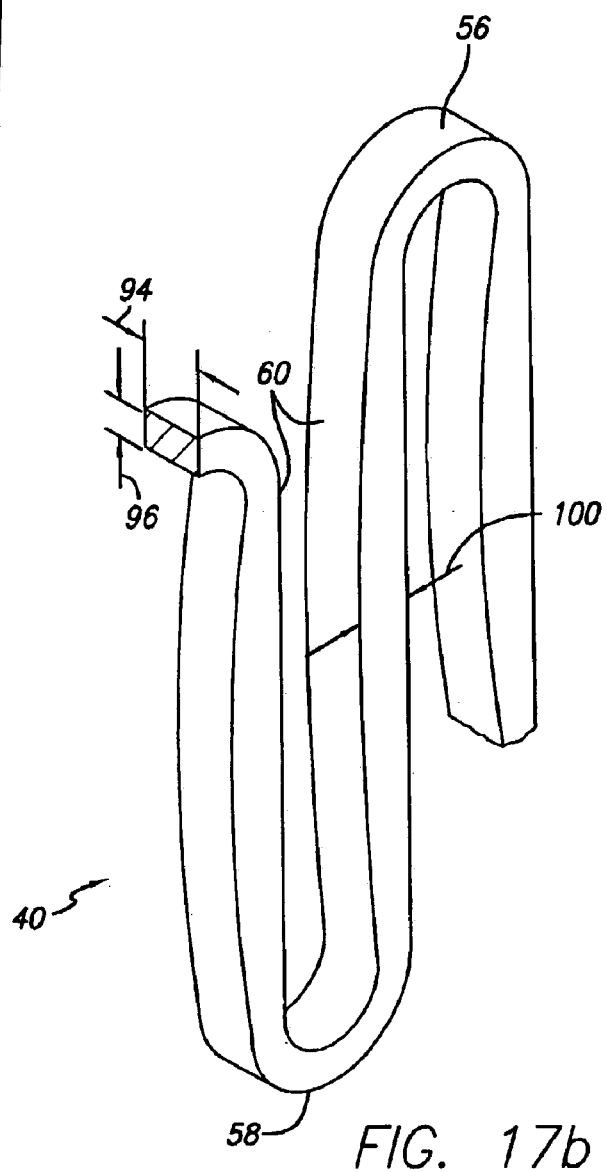
FIG. 17B is an enlarged view depicting another embodiment of a portion of a cylindrical ring having flexible portions and stable portions.

It may be desirable in some embodiments to increase the strength of some portions of the stent while maintaining flexibility of the stent. With reference to FIGS. 17A, 17B, one embodiment of the invention includes flexing portions and stable portions. The flexing portions maintain flexibility and the stable portions have increased strength. For instance, the flexing portions of the stent may include the peaks 56 and the valleys 58 of the cylindrical rings 40. Accordingly, the peaks and valleys may have a nominal radial thickness 94 and a nominal width 96 which maintains flexibility of the cylindrical rings at the peaks and valleys. The stable portions of the stent may include the struts 60 between the peaks and valleys. Hence, the struts between the peaks and valleys may include a greater-than-nominal radial thickness 98 (FIG. 17A) or width 100 (FIG. 17B), or both radial thickness and width, to increase the strength of the struts. Although the example disclosed refers to particular portions of the stent having the varying radial thickness or width, the portions of the stent including the nominal radial thickness and the greater-than-nominal radial thickness may vary as desired to attain varying degrees of strength within the stent.

The aforementioned features of the stent 10, and the varying embodiments thereof as depicted in FIGS. 10–18, may be incorporated into stents of the following embodiments. For the sake of clarity, structural elements in the following embodiments that correspond with those in FIGS. 1–18 use the same reference numbers.

Figure 19:
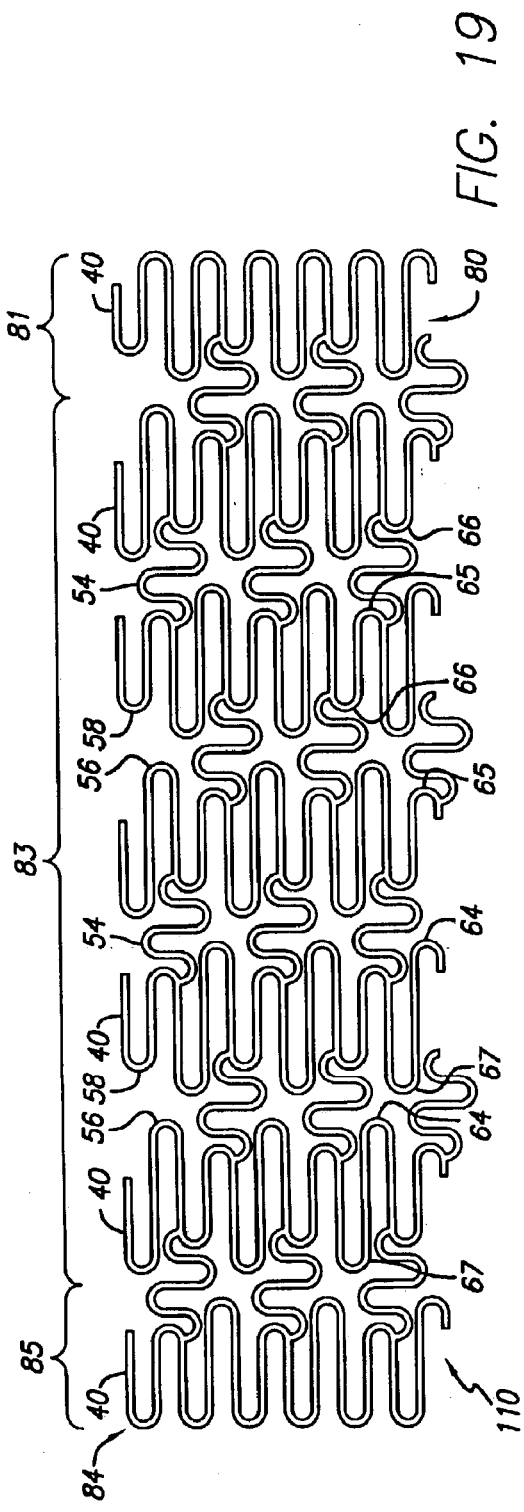
FIG. 19 is a plan view of a flattened stent of the invention which illustrates the pattern of another embodiment of the stent.

Referring to FIG. 19, another embodiment of the invention, which is similar to the embodiment depicted in FIG. 4, is shown. In this embodiment, however, the stent 110 includes the cylindrical rings 40 with the peaks 56 at the distal position 65 circumferentially aligned with the peaks at the proximal position 64 on the adjacent cylindrical ring. Conversely, the valleys 58 at the distal position 67 are circumferentially aligned with the valleys at the proximal position 66 of the adjacent cylindrical ring. In this manner, the peaks 56 of one cylindrical ring 40 are circumferentially offset from the valleys 58 of the proximally adjacent cylindrical ring. Yet, undulating links 54 couple adjacent cylindrical rings 40 to each other with the distal end of each link being coupled to a peak 56 at the distal position 65 of one ring, and the proximal end of each link being coupled to the proximally adjacent ring 40 at the circumferentially adjacent valley 58 at the proximal position 66. In one embodiment, the distal end of the link 54 is coupled at a position a distance from the apex of the peak 56, on the side of the peak which is nearest to the valley 58 to which the proximal end of the link is coupled. Similarly, the proximal end of the link 54 is coupled at a position a distance from the apex of the valley 58, on the side of the valley 58 which is nearest to the peak to which the distal end of the link is coupled. However, in other embodiments, the proximal and distal ends of the links 54 may be coupled to the same side of the apices of the peaks 56 and valleys 58, as depicted in FIG. 18, or coupled to the apices of the peaks and valleys, as depicted in FIG. 15. Also, the links 86 positioned between the proximal ring 80 and the central region 83, and the links 86 positioned between the distal ring 84 and the central region, may include the straight configuration 88 of FIG. 16.

Figure 20:
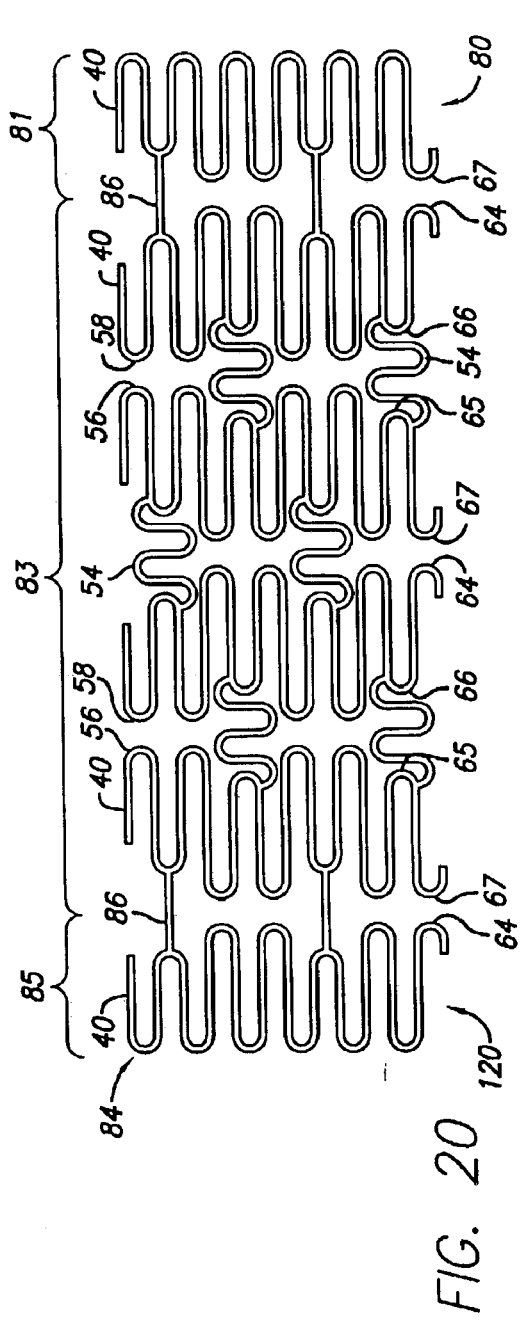
FIG. 20 is a plan view of a flattened stent of the invention which illustrates the pattern of another embodiment of the stent.

With reference to FIG. 20, a further embodiment of the invention is shown which is similar to the embodiment depicted in FIG. 4. In this embodiment, however, the stent 120 includes the cylindrical rings 40 with pairs of peaks 56 at the proximal position 64 positioned circumferentially adjacent each other. Each pair of adjacent peaks at the proximal position is separated from the next circumferentially adjacent pair of peaks at the proximal position by a single peak at the distal position 65. Similarly, pairs of valleys at the distal position 67 are positioned circumferentially adjacent each other with each pair of adjacent valleys at the distal position being separated from the next circumferentially adjacent pair of valleys at the distal position by a single valley at the proximal position 66. Each peak at the distal position is positioned between a circumferentially adjacent pair of valleys at the distal position while each valley at the proximal position is positioned between a circumferentially adjacent pair of peaks at the proximal position. Adjacent cylindrical rings are positioned such that the peaks at the distal position on one ring are circumferentially aligned with the valleys at the proximal position of the adjacent cylindrical ring.

With continued reference to FIG. 20, the undulating links 54 couple adjacent cylindrical rings to each other with the distal end of each link being coupled to a peak 56 at the distal position 65 on one ring, and the proximal end of each link being coupled to the proximally adjacent ring at the circumferentially aligned valley 58 at the proximal position 66. In one embodiment, the distal end of each link is coupled at a position a distance from the apex of the peak and the proximal end of the link is coupled at a position a distance from the apex of the valley. The proximal and distal ends of the link may be coupled to opposing sides of the peak and valley, as depicted in FIG. 12. However, in other embodiments, the proximal and distal ends of the links may be coupled to the same side of the apices of the peaks and valleys, as depicted in FIG. 18, or coupled to the apices of the peaks and valleys, as depicted in FIG. 15. Also, the links 86 positioned between the proximal ring 80 and the central region 83, and the links positioned between the distal ring 84 and the central region, may include the straight configuration 88 depicted FIG. 16.

Referring to FIG. 21, an additional embodiment of the invention is shown which is similar to the embodiment 120 depicted in FIG. 20. As with the stent 120 of FIG. 20, the stent 130 includes the cylindrical rings 40 with pairs of peaks 56 at the proximal position 64 positioned circumferentially adjacent each other. Each pair of adjacent peaks at the proximal position is separated from the next circumferentially adjacent pair of peaks at the proximal position by a single peak at the distal position 65. Similarly, pairs of valleys at the distal position 67 are positioned circumferentially adjacent each other with each pair of adjacent valleys at the distal position being separated from the next circumferentially adjacent pair of valleys at the distal position by a single valley at the proximal position 66. Each peak at the distal position is positioned between a circumferentially adjacent pair of valleys at the distal position while each valley at the proximal position is positioned between a circumferentially adjacent pair of peaks at the proximal position. However, as with the stent 110 of FIG. 19, adjacent cylindrical rings of the stent 130 are positioned such that the peaks at the distal position on one ring are circumferentially aligned with the peaks at the proximal position of the adjacent cylindrical ring. Conversely, valleys at the proximal position on one ring are circumferentially aligned with the valleys at the distal position of the adjacent cylindrical ring.

With continued reference to FIG. 21, the undulating links 54 couple adjacent cylindrical rings to each other with the distal end of each link being coupled to a peak 56 at the distal position 65 of one ring, and the proximal end of each link being coupled to the proximally adjacent ring at the circumferentially adjacent valley 58 at the proximal position 66. In one embodiment, the distal end of the link is coupled at a position a distance from the apex of the peak, on the side of the peak which is nearest to the valley to which the proximal end of the link is coupled. Similarly, the proximal end of the link is coupled at a position a distance from the apex of the valley, on the side of the peak which is nearest to the peak to which the distal end of the link is coupled. However, in other embodiments, the proximal and distal ends of the links may be coupled to the same side of the apices of the peaks and valleys, as depicted in FIG. 18, or coupled to the apices of the peaks and valleys, as depicted in FIG. 15. Also, the links 86 positioned between the proximal ring 80 and the central region 83, and the links positioned between the distal ring 84 and the central region, may include the straight configuration 88 of FIG. 16.

Referring to FIG. 22, another embodiment of the invention is shown which is similar to the embodiment 120 depicted in FIG. 20. As with the stent 120 of FIG. 20, the stent 140 includes the cylindrical rings 40 with pairs of peaks 56 at the proximal position 64 positioned circumferentially adjacent each other. Each pair of adjacent peaks at the proximal position is separated from the next circumferentially adjacent pair of peaks at the proximal position by a single peak at the distal position 65. Similarly, pairs of valleys 58 at the distal position 67 are positioned circumferentially adjacent each other with each pair of adjacent valleys at the distal position being separated from the next circumferentially adjacent pair of valleys at the distal position by a single valley at the proximal position 66. However, positioned between each circumferentially adjacent pair of valleys at the distal position is a peak at the proximal position and positioned between each circumferentially adjacent pair of peaks at the proximal position is a valley at the distal position. In this manner, each peak 56 at the distal position is positioned circumferentially adjacent to a valley at the proximal position and is coupled thereto by a strut 60. As with the stent 120 of FIG. 20, adjacent cylindrical rings of the stent 140 are positioned such that the peaks at the distal position 67 on one ring are circumferentially aligned with the valleys at the proximal position 66 of the proximally adjacent cylindrical ring. Likewise, peaks at the proximal position on one ring are circumferentially aligned with the valleys at the distal position on the proximally adjacent ring.

With continued reference to FIG. 22, the stent 140 includes the undulating links 54 and links 142 having at least one curved portion 144 and straight portions. The undulating links 54 couple adjacent cylindrical rings 40 to each other with the distal end of each link being coupled to a peak 56 at the distal position 65 of one ring, and the proximal end of each link being coupled to the proximally adjacent ring at the circumferentially aligned valley 58 at the proximal position 66. In one embodiment, the distal end of the undulating link is coupled at a position a distance from the apex of the peak and the proximal end of the link is coupled at a position a distance from the apex of the valley. The proximal and distal ends of the undulating link may be coupled to opposing sides of the peak and valley, as depicted in FIG. 12. However, in other embodiments, the proximal and distal ends of the undulating links may be coupled to the same side of the apices of the peaks and valleys, as depicted in FIG. 18, or coupled to the apices of the peaks and valleys, as depicted in FIG. 15. Also, the links 86 positioned between the proximal valleys of the proximal ring 80 and the central region 83, and the links positioned between the distal peaks of the distal ring 84 and the central region, may include the straight configuration 88 of FIG. 16.

As stated above, the stent 140 (FIG. 22) also includes the links 142 having the at least one curved portion 144 and straight portions. The straight portions of the link 142 include a first, proximal arm 146 and a second, distal arm 148 which extend substantially longitudinally and parallel to the longitudinal axis of the stent. The at least one curved portion is positioned between the first and second arms. The links 142 couple adjacent cylindrical rings 40 with the second, distal arm of each link being coupled to a valley 58 which is positioned between a circumferentially adjacent pair of peaks 56 at the proximal position 64. The first, proximal arm of each link is coupled to the circumferentially aligned peak which is positioned between a circumferentially adjacent pair of valleys at the distal position 67 of the proximally adjacent ring. The link 142 is configured such that the at least one curved portion 144 is positioned between the adjacent pair of rings.

Figure 23:
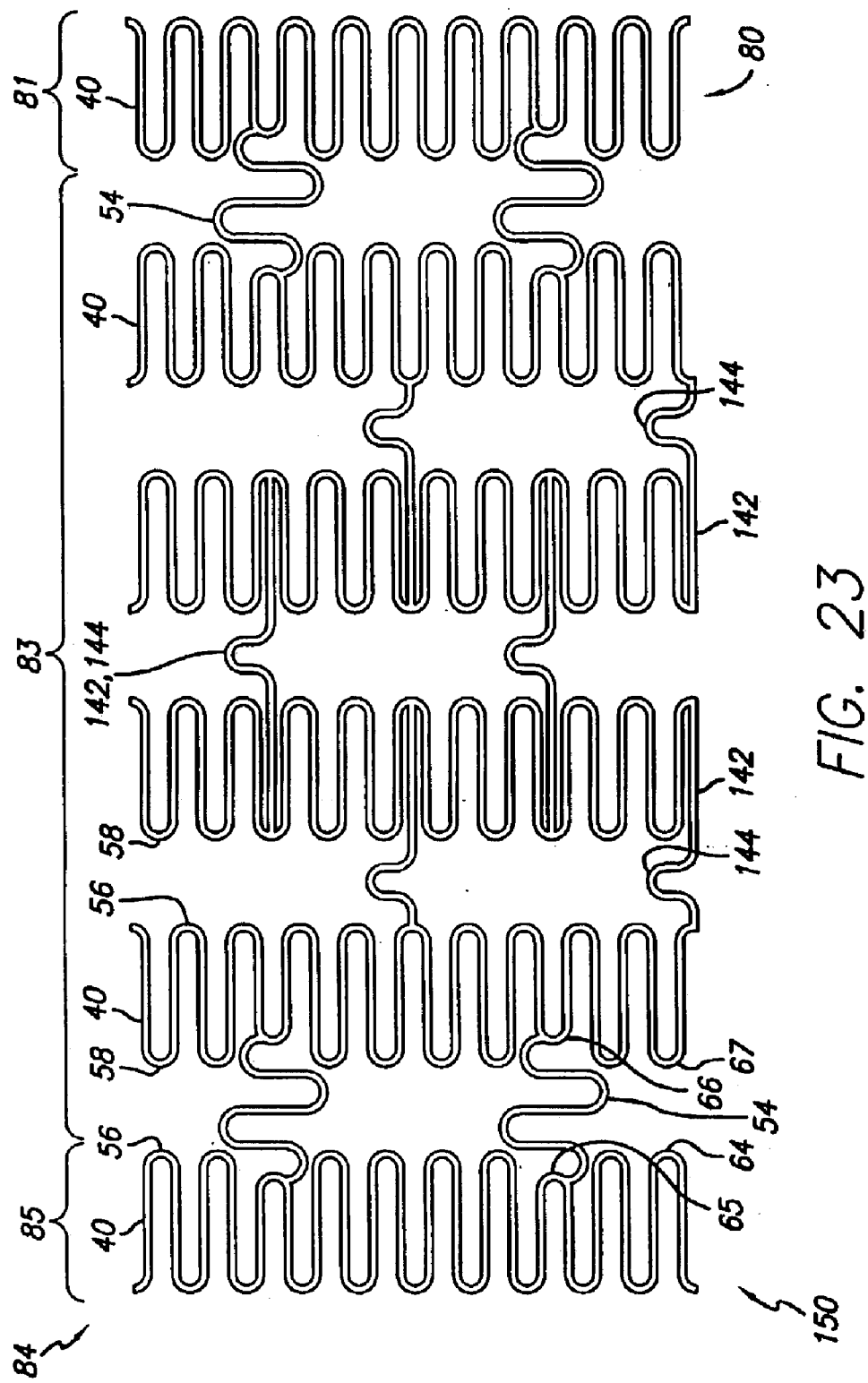
FIG. 23 is a plan view of a flattened stent of the invention which illustrates the pattern of another embodiment of the stent.

Referring to FIG. 23, a further embodiment of the invention includes a stent 150 having a plurality of cylindrical rings 40 with peaks 56 at the proximal end and valleys 58 at the distal end of each ring. Each of the peaks of a cylindrical ring may be longitudinally aligned with each other along the longitudinal axis of the stent, or longitudinally offset between a first, proximal position 64 and a second, distal position 65. Similarly, each of the valleys of a cylindrical ring may be longitudinally aligned with each other along the longitudinal axis of the stent, or longitudinally offset between a first, proximal position 66 and a second, distal position 67. The radii of individual peaks and valleys are variable such that when the stent is expanded to the second, implanted diameter, the circumferential distance between adjacent peaks and adjacent valleys is variable about the circumference of the cylindrical rings. Adjacent cylindrical rings may be positioned such that at least one peak on a distally adjacent cylindrical ring is circumferentially aligned with a valley on the proximally adjacent cylindrical ring; at least one peak on a distally adjacent cylindrical ring is circumferentially aligned with a peak on the proximally adjacent cylindrical ring; at least one valley on a distally adjacent cylindrical ring is circumferentially aligned with a valley on the proximally adjacent cylindrical ring; and at least one valley on a distally adjacent cylindrical ring is circumferentially aligned with a peak on the proximally adjacent cylindrical ring.

With continued reference to FIG. 23, the stent may include the undulating links 54 and the links 142 having at least one curved portion 144 and straight portions, with each pair of adjacent cylindrical rings being coupled together with either one or both types of links. More particularly, at least one pair of adjacent cylindrical rings 40 may be coupled together by at least one undulating link 54 and at least one pair of adjacent cylindrical rings may be coupled together by at least one link 142 having at least one curved portion 144 and straight portions. In one embodiment, the undulating links 54 couple adjacent cylindrical rings between a peak on the distally adjacent ring and a circumferentially aligned valley on the proximally adjacent ring. The distal end of the undulating link may be coupled at a position a distance from the apex of the peak and the proximal end of the link may be coupled at a position a distance from the apex of the valley. The proximal and distal ends of the undulating link may be coupled to opposing sides of the peak and valley, as depicted in FIG. 12. However, in other embodiments, the proximal and distal ends of the undulating links may be coupled to the same side of the apices of the peaks and valleys, as depicted in FIG. 18, or coupled to the apices of the peaks and valleys, as depicted in FIG. 15. Also, the links 86 positioned between the valleys of the proximal ring 80 and the circumferentially aligned peaks of the distally adjacent ring of the central region 83, and the links positioned between the peaks of the distal ring 84 and the circumferentially aligned valleys of the proximally adjacent ring of the central region, may include the straight configuration 88 of FIG. 16.

Figure 24:
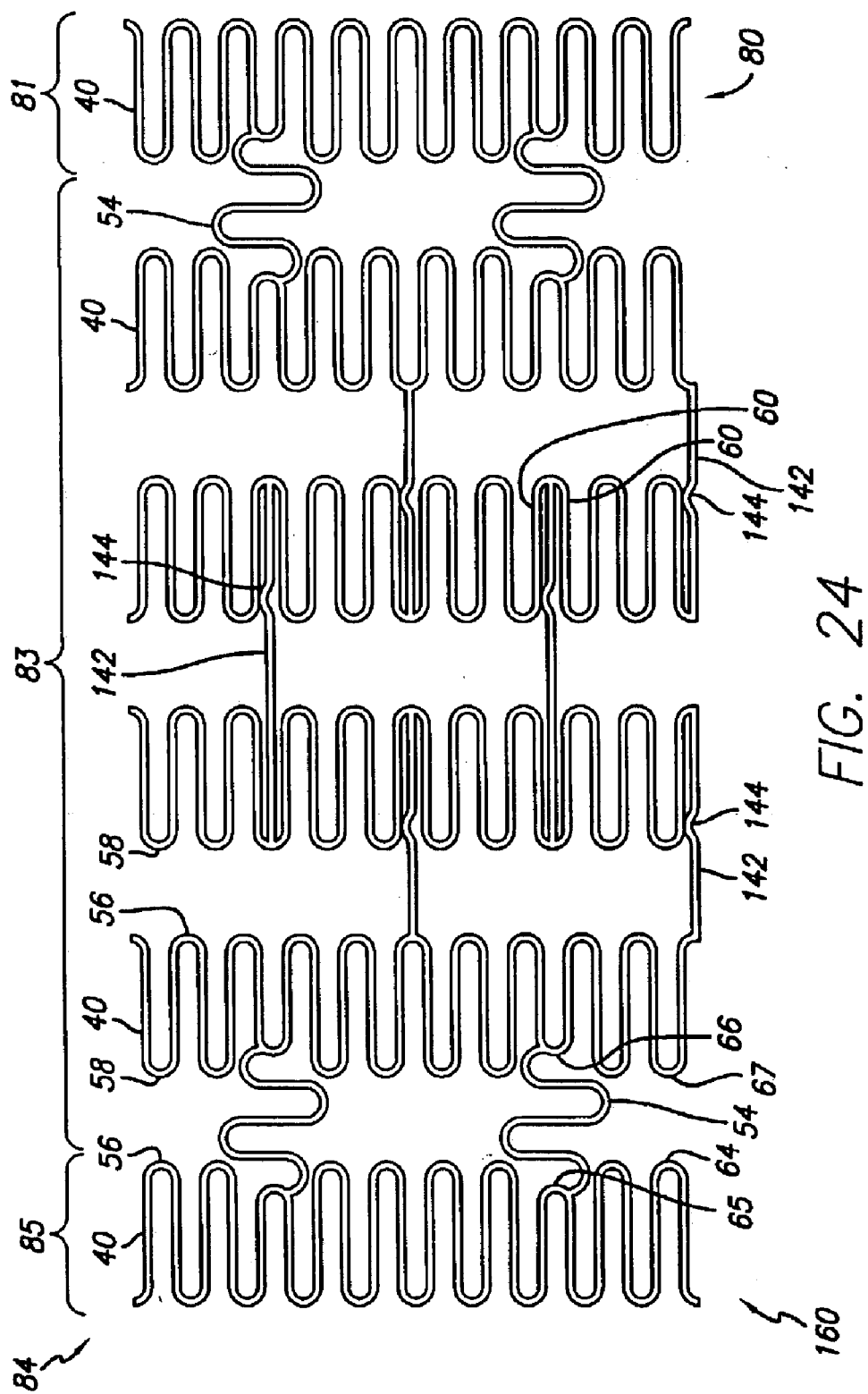
FIG. 24 is a plan view of a flattened stent of the invention which illustrates the pattern of another embodiment of the stent.

With further reference to FIG. 23, at least one pair of adjacent cylindrical rings may be coupled together by at least one of the links 142 having at least one curved portion 144 and straight portions between a peak 56 on the distally adjacent ring and a circumferentially aligned peak on the proximally adjacent ring. Similarly, at least one pair of adjacent cylindrical rings may be coupled together by at least one of the links 142 having at least one curved portion 144 and straight portions between a valley 58 on the distally adjacent ring and a cylindrically aligned valley on the proximally adjacent ring. Further, at least one pair of adjacent cylindrical rings may be coupled together by at least one of the links 142 having at least one curved portion 144 and straight portions between a valley on the distally adjacent ring and a cylindrically aligned peak on the proximally adjacent ring. In one embodiment, the curved portion 144 of the links 142 may be positioned between adjacent cylindrical rings 40, as depicted in FIG. 23. In another embodiment of the invention, a stent 160 (FIG. 24) includes the curved portion 144 of the links 142 being positioned between the struts 60 of at least one of the adjacent cylindrical rings to which the link is coupled.

Figure 25:
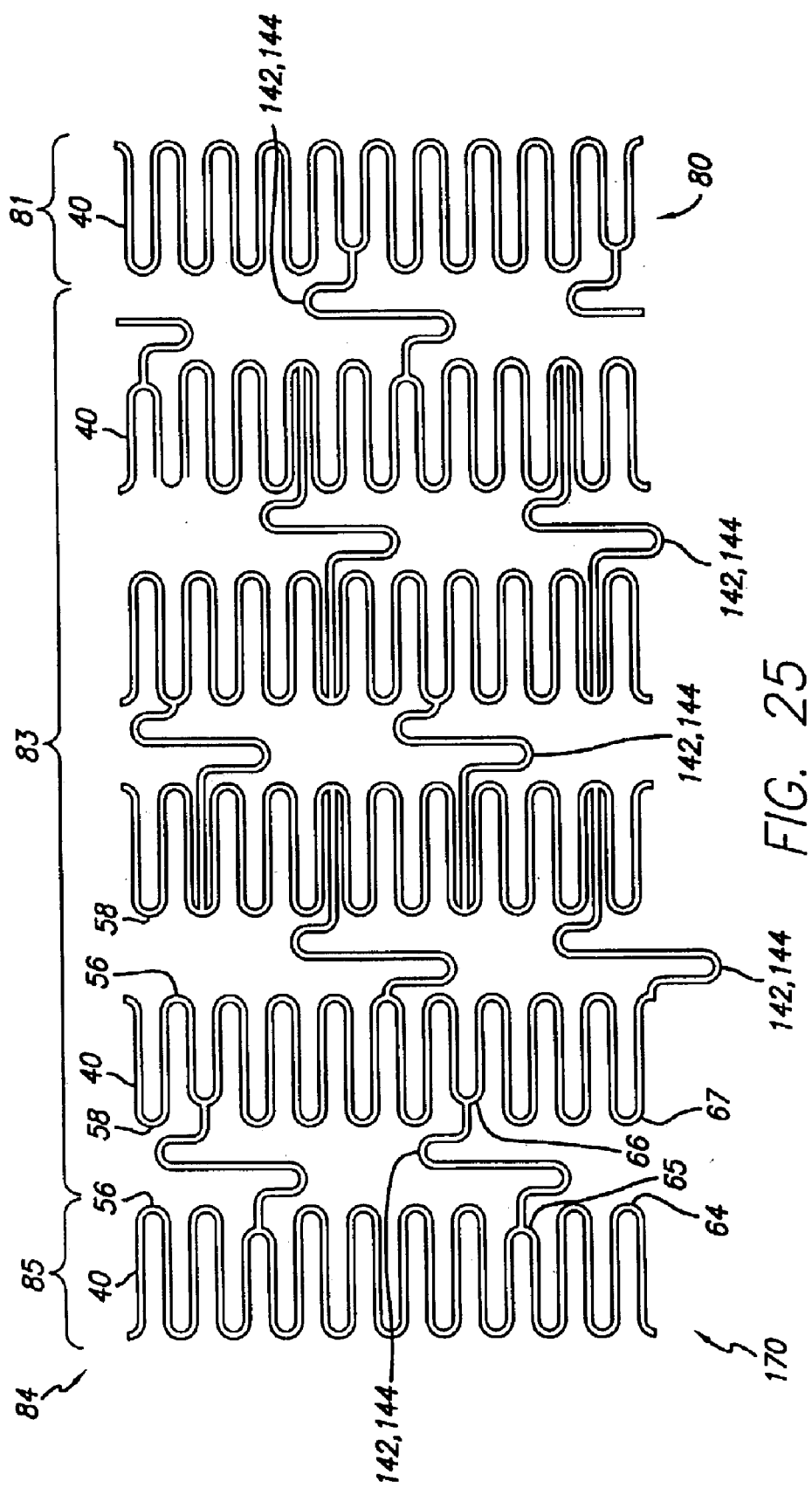
FIG. 25 is a plan view of a flattened stent of the invention which illustrates the pattern of another embodiment of the stent.

Referring to FIG. 25, a further embodiment of the invention includes a stent 170 having the links 142 having at least one curved portion 144 and straight portions coupling nonaligned peaks 56 and valleys 58 on pairs of adjacent cylindrical rings 40. In other words, the links 142 may couple a peak on one ring to a circumferentially nonaligned peak or valley on the proximally adjacent ring, or couple a valley on one ring to a circumferentially nonaligned peak or valley on the proximally adjacent ring.

Any portion of the disclosed stent can be made from a metal alloy or from a polymer. For example, the cylindrical rings can be made from a metal alloy while the connecting links can be made from a metal alloy or a polymer. Typically, if the links are made from a polymer, the stent will be more longitudinally flexible than if the links were made from a metal alloy.

Exemplary of the metallic material used in forming the cylindrical rings and links of the stent is stainless steel, titanium, nickel titanium, tantalum, gold, cobalt-chromium, platinum, palladium, and iradium. Other metals, metal alloys and polymers may also be used to form the present invention stent.

Exemplary of the biocompatible polymer material used in forming the rings or the the links includes the group of polymers consisting of polyurethanes, polyetherurethanes, polyesterurethanes, silicone, thermoplastic elastomer (C-flex), polyether-amide thermoplastic elastomer (Pebax), fluoroelastomers, fluorosilicone elastomer, styrene-butadiene rubber, butadiene-styrene rubber, polyisoprene, neoprene (polychloroprene), ethylene-propylene elastomer, chlorosulfonated polyethylene elastomer, butyl rubber, polysulfide elastomer, polyacrylate elastomer, nitrile rubber, a family of elastomers composed of styrene, ethylene, propylene, aliphatic polycarbonate polyurethane, polymers augmented with antioxidants, polymers augmented with image enhancing materials, polymers having a proton (H+) core, polymers augmented with protons (H+), butadiene and isoprene (Kraton) and polyester thermoplastic elastomer (Hytrel), polyethylene, polylactic acid (PLA), polyglycolic acid (PGA), and polylactic-co-glycolic acid (PLGA).

The stent of the invention also can be coated with a drug or therapeutic agent 180, as shown in FIGS. 26–27. Further, it is well known that the stent (when made from a metal) may require a primer material coating such as a polymer to provide a substrate on which a drug or therapeutic agent is coated since some drugs and therapeutic agents do not readily adhere to a metallic surface. The drug or therapeutic agent can be combined with a coating or other medium used for controlled release rates of the drug or therapeutic agent. Examples of therapeutic agents or drugs that are suitable for use with the polymeric materials include sirolimus, everolimus, actinomycin D (ActD), taxol, paclitaxel, or derivatives and analogs thereof. Examples of agents include other antiproliferative substances as well as antineoplastic, antiinflammatory, antiplatelet, anticoagulant, antifibrin, antithrombin, antimitotic, antibiotic, and antioxidant substances. Examples of antineoplastics include taxol (paclitaxel and docetaxel). Further examples of therapeutic drugs or agents that can be combined with the polymeric materials include antiplatelets, anticoagulants, antifibrins, antithrombins, and antiproliferatives. Examples of antiplatelets, anticoagulants, antifibrins, and antithrombins include, but are not limited to, sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen located in Cambridge, Mass.), and 7E-3B® (an antiplatelet drug from Centocor located in Malvern, Pa.). Examples of antimitotic agents include methotrexate, azathioprine, vincristine, vinblastine, fluorouracil, adriamycin, and mutamycin. Examples of cytostatic or antiproliferative agents include angiopeptin (a somatostatin analog from Ibsen located in the United Kingdom), angiotensin converting enzyme inhibitors such as Captopril® (available from Squibb located in New York, N.Y.), Cilazapril® (available from Hoffman-LaRoche located in Basel, Switzerland), or Lisinopril® (available from Merck located in Whitehouse Station, N.J.); calcium channel blockers (such as Nifedipine), colchicine, fibroblast growth factor (FGF) antagonists, fish oil (omega 3-fatty acid), histamine antagonists, Lovastatin® (an inhibitor of HMG-CoA reductase, a cholesterol lowering drug from Merck), methotrexate, monoclonal antibodies (such as platelet-derived growth factor (PDGF) receptors), nitroprusside, phosphodiesterase inhibitors, prostaglandin inhibitor (available from GlaxoSmithKline located in United Kingdom), Seramin (a PDGF antagonist), serotonin blockers, steroids, thioprotease inhibitors, triazolopyrimidine (a PDGF antagonist), and nitric oxide. Other therapeutic drugs or agents which may be appropriate include alpha-interferon, genetically engineered epithelial cells, and dexamethasone.

While the foregoing therapeutic agents have been used to prevent or treat restenosis, they are provided by way of example and are not meant to be limiting, since other therapeutic drugs may be developed which are equally applicable for use with the present invention. The treatment of diseases using the above therapeutic agents are known in the art. Furthermore, the calculation of dosages, dosage rates and appropriate duration of treatment are previously known in the art.

Representative examples of polymers that can be used to coat a stent in accordance with the present invention include ethylene vinyl alcohol copolymer (commonly known by the generic name EVOH or by the trade name EVAL), poly (hydroxyvalerate); poly(L-lactic acid); polycaprolactone; poly(lactide-coglycolide); poly(hydroxybutyrate); poly (hydroxybutyrate-co-valerate); polydioxanone; polyorthoester; polyanhydride; poly(glycolic acid); poly(D,L-lactic acid); poly(glycolicacid-co-trimethylene carbonate); polyphosphoester; polyphosphoester urethane; poly(amino acids); cyanoacrylates; poly(trimethylene carbonate); poly (iminocarbonate); copoly(ether-esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; polybutylmethacrylate; rayon; rayon-triacetate; poly(glycerol-sebacate); cellulose acetate; cellulose butyrate; cellulose acetate butyrate; cellophane; cellulose nitrate; cellulose propionate; cellulose ethers; and carboxymethyl cellulose.

"Solvent" is a liquid substance or composition that is compatible with the polymer and is capable of dissolving the polymer at the concentration desired in the composition. Representative examples of solvents include chloroform, acetone, water (buffered saline), dimethylsulfoxide (DMSO), propylene glycol methyl ether (PM,) isopropylalcohol (IPA), n-propylalcohol, methanol, ethanol, tetrahydrofuran (THF), dimethylformamide (DMF), dimethyl acetamide (DMAC), benzene, toluene, xylene, hexane, cyclohexane, heptane, octane, pentane, nonane, decane, decalin, ethyl acetate, butyl acetate, isobutyl acetate, isopropyl acetate, butanol, diacetone alcohol, benzyl alcohol, 2-butanone, cyclohexanone, dioxane, methylene chloride, carbon tetrachloride, tetrachloroethylene, tetrachloro ethane, chlorobenzene, 1,1,1-trichloroethane, formamide, hexafluoroisopropanol, 1,1,1-trifluoroethanol, and hexamethyl phosphoramide and a combination thereof. The therapeutic substance contained in the coating can be for inhibiting the activity of vascular smooth muscle cells. More specifically, the therapeutic substance can be aimed at inhibiting abnormal or inappropriate migration and/or proliferation of smooth muscle cells for the inhibition of restenosis. The therapeutic substance can also include any active agent capable of exerting a therapeutic or prophylactic effect in the practice of the present invention. For example, the therapeutic substance can be for enhancing wound healing in a vascular site or improving the structural and elastic properties of the vascular site.

Referring again to FIG. 26, it may be desirable to deposit a higher amount of the drug 180 on the links 182 of a stent to improve uniformity of the drug distribution into the vessel wall through the stent region. It may also be desirable to include a higher amount of the drug 180 on the proximal 188 and distal 190 rings of the stent to reduce the amount of restenosis at the edges of the stent, or for other purposes. Micro depots 184 (FIGS. 28 and 30), such as apertures or indentations, or micro channels 186 (FIGS. 29 and 31) may be positioned along the links (FIGS. 28 and 29), distal ring and proximal ring (FIGS. 30 and 31) at the outer surface of the stent to increase the amount of drug deposited onto the stent in those regions.

The stent 10 of the present invention can be made in many ways. One method of making the stent is to cut a tubular member, such as stainless steel tubing to remove portions of the tubing in the desired pattern for the stent, leaving relatively untouched the portions of the metallic tubing which are to form the stent. In accordance with the invention, it is preferred to cut the tubing in the desired pattern by means of a machine-controlled laser as is well known in the art.

After laser cutting the stent pattern the stents are preferably electrochemically polished in an acidic aqueous solution such as a solution of ELECTRO-GLO#300, sold by ELECTRO-GLO Co., Inc. in Chicago, Ill., which is a mixture of sulfuric acid, carboxylic acids, phosphates, corrosion inhibitors and a biodegradable surface active agent. Other electropolishing solutions are well known in the art. The stents may be further treated if desired, for example by applying a biocompatible coating.

Other methods of forming the stent of the present invention can be used, such as chemical etching; electric discharge machining; laser cutting a flat sheet and rolling it into a cylinder; and the like, all of which are well known in the art at this time. The stent of the present invention also can be made from metal alloys other than stainless steel, such as shape memory alloys. Shape memory alloys are well known and include, but are not limited to, nickel-titanium and nickel/titanium/vanadium. Any of the shape memory alloys can be formed into a tube and laser cut in order to form the pattern of the stent of the present invention. As is well known, the shape memory alloys of the stent of the present invention can include the type known as thermoelastic martensitic transformation, or display stress-induced martensite. These types of alloys are well known in the art and need not be further described here.

Importantly, a stent formed of shape memory alloys, whether the thermoelastic or the stress-induced martensite-type, can be delivered using a balloon catheter of the type described herein, or in the case of stress induced martensite, be delivered via a catheter without a balloon or a sheath catheter.

While the invention has been illustrated and described herein, in terms of its use as an intravascular stent, it will be apparent to those skilled in the art that the stent can be used in other body lumens. Further, particular sizes and dimensions, number of peaks per ring, materials used, and the like have been described herein and are provided as examples only. Other modifications and improvements may be made without departing from the scope of the invention.

What is claimed:

1. An intravascular stent for use in a body lumen, comprising:

a plurality of cylindrical rings including a proximal ring, at least one central ring and a distal ring, each cylindrical ring having a strut pattern, a proximal end and a distal end, the proximal end and the distal end defining a ring length, the cylindrical rings being coaxially aligned along a common longitudinal axis forming the stent and radially expandable with a first delivery diameter and a second implanted diameter; and a plurality of links coupling adjacent cylindrical rings;

wherein each strut pattern of the cylindrical rings including an undulating pattern of U-shaped portions forming peaks at the proximal end of the cylindrical ring and valleys at the distal end of the cylindrical ring with struts extending therebetween;

the adjacent valleys of the proximal ring alternating between a first, proximal position along the longitudinal axis of the stent and a second, distal position along the longitudinal axis of the stent;

the adjacent peaks of the at least one central ring alternating between a first, proximal position along the longitudinal axis of the stent and a second, distal position along the longitudinal axis of the stent and adjacent valleys of the at least one central ring alternating between a first, proximal position along the longitudinal axis of the stent and a second, distal position along the longitudinal axis of the stent;

the adjacent peaks of the distal ring alternating between a first, proximal position along the longitudinal axis of the stent and a second, distal position along the longitudinal axis of the stent;

the peaks of each cylindrical ring being circumferentially aligned with the valleys of the adjacent cylindrical ring; and wherein the links couple alternating peaks on one cylindrical ring to circumferentially aligned valleys on the proximally adjacent cylindrical ring.

2. The stent of claim 1, wherein:

the peaks positioned at the second, distal position being circumferentially aligned with the valleys positioned at the first, proximal position of the proximally adjacent cylindrical ring; and the links coupling the peaks positioned at the second, distal position on one cylindrical ring to the valleys positioned at the first, proximal position on the proximally adjacent cylindrical ring.

3. The stent of claim 2, wherein a distal end of each link being coupled to the apex of a peak positioned at the second, distal position on one cylindrical ring and a proximal end of the link being coupled to the apex of the circumferentially aligned valley positioned at the first, proximal position on the proximally adjacent cylindrical ring.

4. The stent of claim 2, wherein a distal end of each link being coupled a distance from the apex of a peak positioned at the second, distal position on one cylindrical ring and a proximal end of the link being coupled a distance from the apex of the circumferentially aligned valley positioned at the first, proximal position on the proximally adjacent cylindrical ring.

5. The stent of claim 4, wherein the distal end and proximal end of the link being coupled to the same side of the respective apices of the peak and valley.

6. The stent of claim 4, wherein the distal end and proximal end of the link being coupled to opposite sides of the respective apices of the peak and valley.

7. The stent of claim 1, wherein:

adjacent peaks of the proximal ring alternating between a first, proximal position along the longitudinal axis of the stent and a second, distal position along the longitudinal axis of the stent; and adjacent valleys of the distal ring alternating between a first, proximal position along the longitudinal axis of the stent and a second, distal position along the longitudinal axis of the stent.

8. The stent of claim 1, wherein:

adjacent peaks of the proximal ring being longitudinally aligned along the longitudinal axis of the stent; and adjacent valleys of the distal ring being longitudinally aligned along the longitudinal axis of the stent.

9. The stent of claim 1, wherein the ring length of each of the central rings being greater than the ring lengths of the proximal ring and the distal ring.

10. The stent of claim 1, wherein:

the links positioned between central rings including an undulating configuration;

the links positioned between the proximal ring and the distally adjacent central ring including a straight configuration; and the links positioned between the distal ring and the proximally adjacent central ring including a straight configuration.

11. The stent of claim 1, wherein the links including an undulating configuration having a plurality of curved portions with struts extending therebetween.

12. The stent of claim 11, wherein the struts of the links including a straight configuration with the struts positioned perpendicular to the longitudinal axis of the stent.

13. The stent of claim 11, wherein the struts of the links including a straight configuration with the struts positioned at an angle to the longitudinal axis of the stent.

14. The stent of claim 11, wherein the struts of the links including a curved configuration.

15. The stent of claim 1, wherein the struts of the cylindrical rings including a straight configuration.

16. The stent of claim 1, wherein the struts of the cylindrical rings including a curved configuration.

17. The stent of claim 1, wherein at least a portion of the stent being coated with a drug.

18. The stent of claim 17, further comprising micro depots positioned along the links at the outer surface of the stent, the drug substantially filling the micro depots.

19. The stent of claim 17, further comprising micro channels positioned along the links at the outer surface of the stent, the drug substantially filling the micro channels.

20. The stent of claim 17, further comprising micro depots positioned along the proximal ring and the distal ring at the outer surface of the stent, the drug substantially filling the micro depots.

21. The stent of claim 17, further comprising micro channels positioned along the proximal ring and the distal ring at the outer surface of the stent, the drug substantially filling the micro channels.

22. The stent of claim 1, further comprising:

flexing portions, wherein at least some of the flexing portions having a nominal radial thickness; and stable portions, wherein at least some of the stable portions having a greater-than-nominal radial thickness.

23. The stent of claim 1, further comprising:

flexing portions, wherein at least some of the flexing portions having a nominal width; and stable portions, wherein at least some of the stable portions having a greater-than-nominal width.

24. An intravascular stent for use in a body lumen, comprising:

a plurality of cylindrical rings including a proximal ring, at least one central ring and a distal ring, each cylindrical ring having a strut pattern, a proximal end and a distal end, the proximal end and the distal end defining a ring length, the cylindrical rings being coaxially aligned along a common longitudinal axis forming the stent and radially expandable with a first delivery diameter and a second implanted diameter; and a plurality of links coupling adjacent cylindrical rings;

wherein each strut pattern of the cylindrical rings including an undulating pattern of U-shaped portions forming peaks at the proximal end of the cylindrical ring and valleys at the distal end of the cylindrical ring with struts extending therebetween;

the adjacent valleys of the proximal ring alternating between a first, proximal position along the longitudinal axis of the stent and a second, distal position along the longitudinal axis of the stent;

the adjacent peaks of the at least one central ring alternating between a first, proximal position along the longitudinal axis of the stent and a second, distal position along the longitudinal axis of the stent and adjacent valleys of the at least one central ring alternating between a first, proximal position along the longitudinal axis of the stent and a second, distal position along the longitudinal axis of the stent;

the adjacent peaks of the distal ring alternating between a first, proximal position along the longitudinal axis of the stent and a second, distal position along the longitudinal axis of the stent;

the peaks positioned at the second, distal position being circumferentially aligned with the valleys positioned at the first, proximal position of the proximally adjacent cylindrical ring; and wherein the links couple the peaks positioned at the second, distal position on one cylindrical ring to the valleys positioned at the first, proximal position on the proximally adjacent cylindrical ring.

25. The stent of claim 24, wherein a distal end of each link being coupled to the apex of a peak positioned at the second, distal position on one cylindrical ring and a proximal end of the link being coupled to the apex of the circumferentially aligned valley positioned at the first, proximal position on the proximally adjacent cylindrical ring.

26. The stent of claim 24, wherein a distal end of each link being coupled a distance from the apex of a peak positioned at the second, distal position on one cylindrical ring and a proximal end of the link being coupled a distance from the apex of the circumferentially aligned valley positioned at the first, proximal position on the proximally adjacent cylindrical ring.

27. The stent of claim 24, wherein:

the links positioned between central rings including an undulating configuration;

the links positioned between the proximal ring and the distally adjacent central ring including a straight configuration; and the links positioned between the distal ring and the proximally adjacent central ring including a straight configuration.

28. An intravascular stent for use in a body lumen, comprising:

a plurality of cylindrical rings including a proximal ring, at least one central ring and a distal ring, each cylindrical ring having a strut pattern, a proximal end and a distal end, the proximal end and the distal end defining a ring length, the cylindrical rings being coaxially aligned along a common longitudinal axis forming the stent and radially expandable with a first delivery diameter and a second implanted diameter; and a plurality of links coupling adjacent cylindrical rings;

wherein each strut pattern of the cylindrical rings including an undulating pattern of U-shaped portions forming peaks at the proximal end of the cylindrical ring and valleys at the distal end of the cylindrical ring with struts extending therebetween;

the adjacent valleys of the proximal ring alternating between a first, proximal position along the longitudinal axis of the stent and a second, distal position along the longitudinal axis of the stent;

the adjacent peaks of the at least one central ring alternating between a first, proximal position along the longitudinal axis of the stent and a second, distal position along the longitudinal axis of the stent and adjacent valleys of the at least one central ring alternating between a first, proximal position along the longitudinal axis of the stent and a second, distal position along the longitudinal axis of the stent;

the adjacent peaks of the distal ring alternating between a first, proximal position along the longitudinal axis of the stent and a second, distal position along the longitudinal axis of the stent;

the peaks of each cylindrical ring being circumferentially aligned with the peaks of the adjacent cylindrical ring; and wherein the links couple alternating peaks on one cylindrical ring to circumferentially adjacent valleys on the proximally adjacent cylindrical ring.

29. The stent of claim 28, wherein:

the peaks positioned at the second, distal position being circumferentially aligned with the peaks positioned at the first, proximal position of the proximally adjacent cylindrical ring; and the links coupling the peaks positioned at the second, distal position on one cylindrical ring to the circumferentially adjacent valleys positioned at the first, proximal position on the proximally adjacent cylindrical ring.

30. The stent of claim 29, wherein a distal end of each link being coupled to the apex of a peak positioned at the second, distal position on one cylindrical ring and a proximal end of the link being coupled to the apex of the circumferentially adjacent valley positioned at the first, proximal position on the proximally adjacent cylindrical ring.

31. The stent of claim 29, wherein a distal end of each link being coupled a distance from the apex of a peak positioned at the second, distal position on one cylindrical ring and a proximal end of the link being coupled a distance from the apex of the circumferentially adjacent valley positioned at the first, proximal position on the proximally adjacent cylindrical ring.

32. The stent of claim 31, wherein the distal end and proximal end of the link being coupled to the same side of the respective apices of the peak and valley.

33. The stent of claim 31, wherein the distal end and proximal end of the link being coupled to opposite sides of the respective apices of the peak and valley.

34. The stent of claim 28, wherein:

adjacent peaks of the proximal ring alternating between a first, proximal position along the longitudinal axis of the stent and a second, distal position along the longitudinal axis of the stent; and adjacent valleys of the distal ring alternating between a first, proximal position along the longitudinal axis of the stent and a second, distal position along the longitudinal axis of the stent.

35. The stent of claim 28, wherein:

adjacent peaks of the proximal ring being longitudinally aligned along the longitudinal axis of the stent; and adjacent valleys of the distal ring being longitudinally aligned along the longitudinal axis of the stent.

36. The stent of claim 28, wherein the ring length of each of the central rings being greater than the ring lengths of the proximal ring and the distal ring.

37. The stent of claim 28, wherein:

the links positioned between central rings including an undulating configuration;

the links positioned between the proximal ring and the distally adjacent central ring including a straight configuration; and the links positioned between the distal ring and the proximally adjacent central ring including a straight configuration.

38. The stent of claim 28, wherein the links including an undulating configuration having a plurality of curved portions with struts extending therebetween.

39. The stent of claim 38, wherein the struts of the links including a straight configuration with the struts positioned perpendicular to the longitudinal axis of the stent.

40. The stent of claim 38, wherein the struts of the links including a straight configuration with the struts positioned at an angle to the longitudinal axis of the stent.

41. The stent of claim 38, wherein the struts of the links including a curved configuration.

42. The stent of claim 28, wherein the struts of the cylindrical rings including a straight configuration.

43. The stent of claim 28, wherein the struts of the cylindrical rings including a curved configuration.

44. The stent of claim 28, wherein at least a portion of the stent being coated with a drug.

45. The stent of claim 44, further comprising micro depots positioned along the links at the outer surface of the stent, the drug substantially filling the micro depots.

46. The stent of claim 44, further comprising micro channels positioned along the links at the outer surface of the stent, the drug substantially filling the micro channels.

47. The stent of claim 44, further comprising micro depots positioned along the proximal ring and the distal ring at the outer surface of the stent, the drug substantially filling the micro depots.

48. The stent of claim 44, further comprising micro channels positioned along the proximal ring and the distal ring at the outer surface of the stent, the drug substantially filling the micro channels.

49. The stent of claim 28, further comprising:

flexing portions, wherein at least some of the flexing portions having a nominal radial thickness; and stable portions, wherein at least some of the stable portions having a greater-than-nominal radial thickness.

50. The stent of claim 28, further comprising:

flexing portions, wherein at least some of the flexing portions having a nominal width; and stable portions, wherein at least some of the stable portions having a greater-than-nominal width.

51. An intravascular stent for use in a body lumen, comprising:

a plurality of cylindrical rings including a proximal ring, at least one central ring and a distal ring, each cylindrical ring having a strut pattern, a proximal end and a distal end, the proximal end and the distal end defining a ring length, the cylindrical rings being coaxially aligned along a common longitudinal axis forming the stent and radially expandable with a first delivery diameter and a second implanted diameter; and a plurality of links coupling adjacent cylindrical rings;

wherein each strut pattern of the cylindrical rings including an undulating pattern of U-shaped portions forming peaks at the proximal end of the cylindrical ring and valleys at the distal end of the cylindrical ring with struts extending therebetween;

the adjacent valleys of the proximal ring alternating between a first, proximal position along the longitudinal axis of the stent and a second, distal position along the longitudinal axis of the stent;

the adjacent peaks of the at least one central ring alternating between a first, proximal position along the longitudinal axis of the stent and a second, distal position along the longitudinal axis of the stent and adjacent valleys of the at least one central ring alternating between a first, proximal position along the longitudinal axis of the stent and a second, distal position along the longitudinal axis of the stent;

the adjacent peaks of the distal ring alternating between a first, proximal position along the longitudinal axis of the stent and a second, distal position along the longitudinal axis of the stent;

the peaks positioned at the second, distal position being circumferentially aligned with the peaks positioned at the first, proximal position of the proximally adjacent cylindrical ring; and wherein the links couple the peaks positioned at the second, distal position on one cylindrical ring to the circumferentially adjacent valleys positioned at the first, proximal position on the proximally adjacent cylindrical ring.

52. The stent of claim 51, wherein a distal end of each link being coupled to the apex of a peak positioned at the second, distal position on one cylindrical ring and a proximal end of the link being coupled to the apex of the circumferentially adjacent valley positioned at the first, proximal position on the proximally adjacent cylindrical ring.

53. The stent of claim 51, wherein a distal end of each link being coupled a distance from the apex of a peak positioned at the second, distal position on one cylindrical ring and a proximal end of the link being coupled a distance from the apex of the circumferentially adjacent valley positioned at the first, proximal position on the proximally adjacent cylindrical ring.

54. The stent of claim 51, wherein:

the links positioned between central rings including an undulating configuration;

the links positioned between the proximal ring and the distally adjacent central ring including a straight configuration; and the links positioned between the distal ring and the proximally adjacent central ring including a straight configuration.

55. An intravascular stent for use in a body lumen, comprising:

a plurality of cylindrical rings including a proximal ring, at least one central ring and a distal ring, each cylindrical ring having a strut pattern, a proximal end and a distal end, the proximal end and the distal end defining a ring length, the cylindrical rings being coaxially aligned along a common longitudinal axis forming the stent and radially expandable with a first delivery diameter and a second implanted diameter; and a plurality of links coupling adjacent cylindrical rings;

wherein each strut pattern of the cylindrical rings including an undulating pattern of U-shaped portions forming peaks at the proximal end of the cylindrical ring and valleys at the distal end of the cylindrical ring with struts extending therebetween;

the valleys of the proximal ring alternating between a single valley at a first, proximal position along the longitudinal axis of the stent and a pair of adjacent valleys at a second, distal position along the longitudinal axis of the stent;

the peaks of the at least one central ring alternating between a pair of adjacent peaks at a first, proximal position along the longitudinal axis of the stent and a single peak at a second, distal position along the longitudinal axis of the stent and valleys of the at least one central ring alternating between a single valley at a first, proximal position along the longitudinal axis of the stent and a pair of adjacent valleys at a second, distal position along the longitudinal axis of the stent, each single peak at the second, distal position being positioned between a pair of adjacent valleys at the second, distal position and each single valley at the first, proximal position being positioned between a pair of adjacent peaks at the first, proximal position;

the peaks of the distal ring alternating between a pair of adjacent peaks at a first, proximal position along the longitudinal axis of the stent and a single peak at a second, distal position along the longitudinal axis of the stent;

the peaks of each cylindrical ring being circumferentially aligned with the valleys of the adjacent cylindrical ring; and wherein the links couple peaks on one cylindrical ring to circumferentially aligned valleys on the proximally adjacent cylindrical ring.

56. The stent of claim 55, wherein:

the peaks positioned at the second, distal position being circumferentially aligned with the valleys positioned at the first, proximal position of the proximally adjacent cylindrical ring; and the links coupling the peaks positioned at the second, distal position on one cylindrical ring to the circumferentially aligned valleys positioned at the first, proximal position on the proximally adjacent cylindrical ring.

57. The stent of claim 56, wherein a distal end of each link being coupled to the apex of a peak positioned at the second, distal position on one cylindrical ring and a proximal end of the link being coupled to the apex of the circumferentially aligned valley positioned at the first, proximal position on the proximally-adjacent cylindrical ring.

58. The stent of claim 56, wherein a distal end of each link being coupled a distance from the apex of a peak positioned at the second, distal position on one cylindrical ring and a proximal end of the link being coupled a distance from the apex of the circumferentially aligned valley positioned at the first, proximal position on the proximally adjacent cylindrical ring.

59. The stent of claim 58, wherein the distal end and proximal end of the link being coupled to the same side of the respective apices of the peak and valley.

60. The stent of claim 58, wherein the distal end and proximal end of the link being coupled to opposite sides of the respective apices of the peak and valley.

61. The stent of claim 55, wherein:

peaks of the proximal ring alternating between a pair of adjacent peaks at a first, proximal position along the longitudinal axis of the stent and a single peak at a second, distal position along the longitudinal axis of the stent, each single peak at the second, distal position being positioned between a pair of adjacent valleys at the second, distal position and each single valley at the first, proximal position being positioned between a pair of adjacent peaks at the first, proximal position;

valleys of the distal ring alternating between a single valley at a first, proximal position along the longitudinal axis of the stent and a pair of adjacent valleys at a second, distal position along the longitudinal axis of the stent, each single valley at the first, proximal position being positioned between a pair of adjacent peaks at the first, proximal position and each single peak at the second, distal position being positioned between a pair of adjacent valleys at the second, distal position.

62. The stent of claim 55, wherein:

adjacent peaks of the proximal ring being longitudinally aligned along the longitudinal axis of the stent; and adjacent valleys of the distal ring being longitudinally aligned along the longitudinal axis of the stent.

63. The stent of claim 55, wherein the ring length of each of the central rings being greater than the ring lengths of the proximal ring and the distal ring.

64. The stent of claim 55, wherein:

the links positioned between central rings including an undulating configuration;

the links positioned between the proximal ring and the distally adjacent central ring including a straight configuration; and the links positioned between the distal ring and the proximally adjacent central ring including a straight configuration.

65. The stent of claim 55, wherein the links including an undulating configuration having a plurality of curved portions with struts extending therebetween.

66. The stent of claim 65, wherein the struts of the links including a straight configuration with the struts positioned perpendicular to the longitudinal axis of the stent.

67. The stent of claim 65, wherein the struts of the links including a straight configuration with the struts positioned at an angle to the longitudinal axis of the stent.

68. The stent of claim 65, wherein the struts of the links including a curved configuration.

69. The stent of claim 55, wherein the struts of the cylindrical rings including a straight configuration.

70. The stent of claim 55, wherein the struts of the cylindrical rings including a curved configuration.

71. The stent of claim 55, wherein at least a portion of the stent being coated with a drug.

72. The stent of claim 71, further comprising micro depots positioned along the links at the outer surface of the stent, the drug substantially filling the micro depots.

73. The stent of claim 71, further comprising micro channels positioned along the links at the outer surface of the stent, the drug substantially filling the micro channels.

74. The stent of claim 71, further comprising micro depots positioned along the proximal ring and the distal ring at the outer surface of the stent, the drug substantially filling the micro depots.

75. The stent of claim 71, further comprising micro channels positioned along the proximal ring and the distal ring at the outer surface of the stent, the drug substantially filling the micro channels.

76. The stent of claim 55, further comprising:

flexing portions, wherein at least some of the flexing portions having a nominal radial thickness; and stable portions, wherein at least some of the stable portions having a greater-than-nominal radial thickness.

77. The stent of claim 55, further comprising:

flexing portions, wherein at least some of the flexing portions having a nominal width; and stable portions, wherein at least some of the stable portions having a greater-than-nominal width.

78. An intravascular stent for use in a body lumen, comprising:

a plurality of cylindrical rings including a proximal ring, at least one central ring and a distal ring, each cylindrical ring having a strut pattern, a proximal end and a distal end, the proximal end and the distal end defining a ring length, the cylindrical rings being coaxially aligned along a common longitudinal axis forming the stent and radially expandable with a first delivery diameter and a second implanted diameter; and a plurality of links coupling adjacent cylindrical rings;

wherein each strut pattern of the cylindrical rings including an undulating pattern of U-shaped portions forming peaks at the proximal end of the cylindrical ring and valleys at the distal end of the cylindrical ring with struts extending therebetween;

the valleys of the proximal ring alternating between a single valley at a first, proximal position along the longitudinal axis of the stent and a pair of adjacent valleys at a second, distal position along the longitudinal axis of the stent;

the peaks of the at least one central ring alternating between a pair of adjacent peaks at a first, proximal position along the longitudinal axis of the stent and a single peak at a second, distal position along the longitudinal axis of the stent and valleys of the at least one central ring alternating between a single valley at a first, proximal position along the longitudinal axis of the stent and a pair of adjacent valleys at a second, distal position along the longitudinal axis of the stent, each single peak at the second, distal position being positioned between a pair of adjacent valleys at the second, distal position and each single valley at the first, proximal position being positioned between a pair of adjacent peaks at the first, proximal position;

the peaks of the distal ring alternating between a pair of adjacent peaks at a first, proximal position along the longitudinal axis of the stent and a single peak at a second, distal position along the longitudinal axis of the stent;

the peaks positioned at the second, distal position being circumferentially aligned with the valleys positioned at the first, proximal position of the proximally adjacent cylindrical ring; and wherein the links couple the peaks positioned at the second, distal position on one cylindrical ring to the circumferentially aligned valleys positioned at the first, proximal position on the proximally adjacent cylindrical ring.

79. The stent of claim 78, wherein a distal end of each link being coupled to the apex of a peak positioned at the second, distal position on one cylindrical ring and a proximal end of the link being coupled to the apex of the circumferentially aligned valley positioned at the first, proximal position on the proximally adjacent cylindrical ring.

80. The stent of claim 78, wherein a distal end of each link being coupled a distance from the apex of a peak positioned at the second, distal position on one cylindrical ring and a proximal end of the link being coupled a distance from the apex of the circumferentially aligned valley positioned at the first, proximal position on the proximally adjacent cylindrical ring.

81. The stent of claim 78, wherein:
the links positioned between central rings including an undulating configuration;
the links positioned between the proximal ring and the distally adjacent central ring including a straight configuration; and
the links positioned between the distal ring and the proximally adjacent central ring including a straight configuration.

82. An intravascular stent for use in a body lumen, comprising:
a plurality of cylindrical rings including a proximal ring, at least one central ring and a distal ring, each cylindrical ring having a strut pattern, a proximal end and a distal end, the proximal end and the distal end defining a ring length, the cylindrical rings being coaxially aligned along a common longitudinal axis forming the stent and radially expandable with a first delivery diameter and a second implanted diameter; and a plurality of links coupling adjacent cylindrical rings;

wherein each strut pattern of the cylindrical rings including an undulating pattern of U-shaped portions forming peaks at the proximal end of the cylindrical ring and valleys at the distal end of the cylindrical ring with struts extending therebetween;

the valleys of the proximal ring alternating between a single valley at a first, proximal position along the longitudinal axis of the stent and a pair of adjacent valleys at a second, distal position along the longitudinal axis of the stent;

the peaks of the at least one central ring alternating between a pair of adjacent peaks at a first, proximal position along the longitudinal axis of the stent and a single peak at a second, distal position along the longitudinal axis of the stent and valleys of the at least one central ring alternating between a single valley at a first, proximal position along the longitudinal axis of the stent and a pair of adjacent valleys at a second, distal position along the longitudinal axis of the stent, each single peak at the second, distal position being positioned between a pair of adjacent valleys at the second, distal position and each single valley at the first, proximal position being positioned between a pair of adjacent peaks at the first, proximal position;

the peaks of the distal ring alternating between a pair of adjacent peaks at a first, proximal position along the longitudinal axis of the stent and a single peak at a second, distal position along the longitudinal axis of the stent;

the peaks of each cylindrical ring being circumferentially aligned with the peaks of the adjacent cylindrical ring; and wherein the links couple peaks on one cylindrical ring to circumferentially adjacent valleys on the proximally adjacent cylindrical ring.

83. The stent of claim 82, wherein:
the peaks positioned at the second, distal position being circumferentially adjacent to the valleys positioned at the first, proximal position of the proximally adjacent cylindrical ring; and
the links coupling the peaks positioned at the second, distal position on one cylindrical ring to the circumferentially adjacent valleys positioned at the first, proximal position on the proximally adjacent cylindrical ring.

84. The stent of claim 83, wherein a distal end of each link being coupled to the apex of a peak positioned at the second, distal position on one cylindrical ring and a proximal end of the link being coupled to the apex of the circumferentially adjacent valley positioned at the first, proximal position on the proximally adjacent cylindrical ring.

85. The stent of claim 83, wherein a distal end of each link being coupled a distance from the apex of a peak positioned at the second, distal position on one cylindrical ring and a proximal end of the link being coupled a distance from the apex of the circumferentially adjacent valley positioned at the first, proximal position on the proximally adjacent cylindrical ring.

86. The stent of claim 85, wherein the distal end and proximal end of the link being coupled to the same side of the respective apices of the peak and valley.

87. The stent of claim 85, wherein the distal end and proximal end of the link being coupled to opposite sides of the respective apices of the peak and valley.

88. The stent of claim 82, wherein:
peaks of the proximal ring alternating between a pair of adjacent peaks at a first, proximal position along the longitudinal axis of the stent and a single peak at a second, distal position along the longitudinal axis of the stent, each single peak at the second, distal position being positioned between a pair of adjacent valleys at the second, distal position and each single valley at the first, proximal position being positioned between a pair of adjacent peaks at the first, proximal position;
valleys of the distal ring alternating between a single valley at a first, proximal position along the longitudinal axis of the stent and a pair of adjacent valleys at a second, distal position along the longitudinal axis of the stent, each single valley at the first, proximal position being positioned between a pair of adjacent peaks at the first, proximal position and each single peak at the second, distal position being positioned between a pair of adjacent valleys at the second, distal position.

89. The stent of claim 82, wherein:
adjacent peaks of the proximal ring being longitudinally aligned along the longitudinal axis of the stent; and
adjacent valleys of the distal ring being longitudinally aligned along the longitudinal axis of the stent.

90. The stent of claim 82, wherein the ring length of each of the central rings being greater than the ring lengths of the proximal ring and the distal ring.

91. The stent of claim 82, wherein:
the links positioned between central rings including an undulating configuration;
the links positioned between the proximal ring and the distally adjacent central ring including a straight configuration; and
the links positioned between the distal ring and the proximally adjacent central ring including a straight configuration.

92. The stent of claim 82, wherein the links including an undulating configuration having a plurality of curved portions with struts extending therebetween.

93. The stent of claim 92, wherein the struts of the links including a straight configuration with the struts positioned perpendicular to the longitudinal axis of the stent.

94. The stent of claim 92, wherein the struts of the links including a straight configuration with the struts positioned at an angle to the longitudinal axis of the stent.

95. The stent of claim 92, wherein the struts of the links including a curved configuration.

96. The stent of claim 82, wherein the struts of the cylindrical rings including a straight configuration.

97. The stent of claim 82, wherein the struts of the cylindrical rings including a curved configuration.

98. The stent of claim 82, wherein at least a portion of the stent being coated with a drug.

99. The stent of claim 98, further comprising micro depots positioned along the links at the outer surface of the stent, the drug substantially filling the micro depots.

100. The stent of claim 98, further comprising micro channels positioned along the links at the outer surface of the stent, the drug substantially filling the micro channels.

101. The stent of claim 98, further comprising micro depots positioned along the proximal ring and the distal ring at the outer surface of the stent, the drug substantially filling the micro depots.

102. The stent of claim 98, further comprising micro channels positioned along the proximal ring and the distal ring at the outer surface of the stent, the drug substantially filling the micro channels.

103. The stent of claim 82, further comprising:
flexing portions, wherein at least some of the flexing portions having a nominal radial thickness; and
stable portions, wherein at least some of the stable portions having a greater-than-nominal radial thickness.

104. The stent of claim 82, further comprising:
flexing portions, wherein at least some of the flexing portions having a nominal width; and
stable portions, wherein at least some of the stable portions having a greater-than-nominal width.

105. An intravascular stent for use in a body lumen, comprising:
a plurality of cylindrical rings including a proximal ring, at least one central ring and a distal ring, each cylindrical ring having a strut pattern, a proximal end and a distal end, the proximal end and the distal end defining a ring length, the cylindrical rings being coaxially aligned along a common longitudinal axis forming the stent and radially expandable with a first delivery diameter and a second implanted diameter; and
a plurality of links coupling adjacent cylindrical rings;
wherein each strut pattern of the cylindrical rings including an undulating pattern of U-shaped portions forming peaks at the proximal end of the cylindrical ring and valleys at the distal end of the cylindrical ring with struts extending therebetween;
the valleys of the proximal ring alternating between a single valley at a first, proximal position along the longitudinal axis of the stent and a pair of adjacent valleys at a second, distal position along the longitudinal axis of the stent;
the peaks of the at least one central ring alternating between a pair of adjacent peaks at a first, proximal position along the longitudinal axis of the stent and a single peak at a second, distal position along the longitudinal axis of the stent and valleys of the at least one central ring alternating between a single valley at a first, proximal position along the longitudinal axis of the stent and a pair of adjacent valleys at a second, distal position along the longitudinal axis of the stent, each single peak at the second, distal position being positioned between a pair of adjacent valleys at the second, distal position and each single valley at the first, proximal position being positioned between a pair of adjacent peaks at the first, proximal position;
the peaks of the distal ring alternating between a pair of adjacent peaks at a first, proximal position along the longitudinal axis of the stent and a single peak at a second, distal position along the longitudinal axis of the stent;
the peaks positioned at the second, distal position being circumferentially adjacent to the valleys positioned at the first, proximal position of the proximally adjacent cylindrical ring; and
wherein the links couple the peaks positioned at the second, distal position on one cylindrical ring to the circumferentially adjacent valleys positioned at the first, proximal position on the proximally adjacent cylindrical ring.

106. The stent of claim 105, wherein a distal end of each link being coupled to the apex of a peak positioned at the second, distal position on one cylindrical ring and a proximal end of the link being coupled to the apex of the circumferentially adjacent valley positioned at the first, proximal position on the proximally adjacent cylindrical ring.

107. The stent of claim 105, wherein a distal end of each link being coupled a distance from the apex of a peak positioned at the second, distal position on one cylindrical ring and a proximal end of the link being coupled a distance from the apex of the circumferentially adjacent valley positioned at the first, proximal position on the proximally adjacent cylindrical ring.

108. The stent of claim 105, wherein:
the links positioned between central rings including an undulating configuration;
the links positioned between the proximal ring and the distally adjacent central ring including a straight configuration; and
the links positioned between the distal ring and the proximally adjacent central ring including a straight configuration.

109. An intravascular stent for use in a body lumen, comprising:
a plurality of cylindrical rings including a proximal ring, at least one central ring and a distal ring, each cylindrical ring having a strut pattern, a proximal end and a distal end, the proximal end and the distal end defining a ring length, the cylindrical rings being coaxially aligned along a common longitudinal axis forming the stent and radially expandable with a first delivery diameter and a second implanted diameter;
a plurality of undulating links coupling a plurality of adjacent cylindrical rings; and
a plurality of links having straight portions and at least one curved portion coupling a plurality of adjacent cylindrical rings;
wherein each strut pattern of the cylindrical rings including an undulating pattern of U-shaped portions forming peaks at the proximal end of the cylindrical ring and valleys at the distal end of the cylindrical ring with struts extending therebetween;
the valleys of the proximal ring alternating between a single valley at a first, proximal position along the longitudinal axis of the stent and a pair of adjacent valleys at a second, distal position along the longitudinal axis of the stent;
the peaks of the at least one central ring alternating between a pair of adjacent peaks at a first, proximal position along the longitudinal axis of the stent and a single peak at a second, distal position along the longitudinal axis of the stent and valleys of the at least one central ring alternating between a single valley at a first, proximal position along the longitudinal axis of the stent and a pair of adjacent valleys at a second, distal position along the longitudinal axis of the stent, a peak at the first, proximal position being positioned between each pair of adjacent valleys at the second, distal position and a valley at the second, distal position being positioned between each pair of adjacent peaks at the first, proximal position, each peak at the distal position being circumferentially adjacent to a valley at the proximal position;
the peaks of the distal ring alternating between a pair of adjacent peaks at a first, proximal position along the longitudinal axis of the stent and a single peak at a second, distal position along the longitudinal axis of the stent;
the peaks of each cylindrical ring being circumferentially aligned with the valleys of the adjacent cylindrical ring;
wherein the undulating links couple a plurality of adjacent cylindrical rings between peaks on one cylindrical ring to circumferentially aligned valleys on the proximally adjacent cylindrical rings; and
wherein the links having the straight portions and at least one curved portion couple a plurality of adjacent cylindrical rings between valleys positioned between circumferentially adjacent pairs of peaks at the proximal position on the distally adjacent cylindrical rings to the circumferentially aligned peaks on the proximally adjacent rings.

110. The stent of claim 109, wherein:
the peaks positioned at the second, distal position of one ring being circumferentially aligned with the valleys positioned at the first, proximal position of the proximally adjacent cylindrical ring;
the undulating links coupling a plurality of adjacent cylindrical rings between the peaks positioned at the second, distal position on one cylindrical ring to the circumferentially aligned valleys positioned at the first, proximal position on the proximally adjacent cylindrical ring; and
the links having the straight portions and at least one curved portion coupling a plurality of adjacent cylindrical rings between valleys positioned between circumferentially adjacent pairs of peaks at the proximal position on one ring to the circumferentially aligned peaks positioned between a circumferentially aligned pair of valleys at the distal position on the proximally adjacent cylindrical ring.

111. The stent of claim 10, wherein a distal end of each undulating link being coupled to the apex of a peak positioned at the second, distal position on one cylindrical ring and a proximal end of the undulating link being coupled to the apex of the circumferentially aligned valley positioned at the first, proximal position on the proximally adjacent cylindrical ring.

112. The stent of claim 110, wherein a distal end of each undulating link being coupled a distance from the apex of a peak positioned at the second, distal position on one cylindrical ring and a proximal end of the undulating link being coupled a distance from the apex of the circumferentially aligned valley positioned at the first, proximal position on the proximally adjacent cylindrical ring.

113. The stent of claim 112, wherein the distal end and proximal end of the undulating link being coupled to the same side of the respective apices of the peak and valley.

114. The stent of claim 112, wherein the distal end and proximal end of the undulating link being coupled to opposite sides of the respective apices of the peak and valley.

115. The stent of claim 109, wherein:
peaks of the proximal ring alternating between a pair of adjacent peaks at a first, proximal position along the longitudinal axis of the stent and a single peak at a second, distal position along the longitudinal axis of the stent, a peak at the first, proximal position being positioned between a pair of adjacent valleys at the second, distal position and a valley at the second, distal position being positioned between a pair of adjacent peaks at the first, proximal position, each peak at the distal position being circumferentially adjacent to a valley at the proximal position; and
valleys of the distal ring alternating between a single valley at a first, proximal position along the longitudinal axis of the stent and a pair of adjacent valleys at a second, distal position along the longitudinal axis of the stent, a valley at the second, distal position being positioned between a pair of adjacent peaks at the first, proximal position and a peak at the first, proximal position being positioned between a pair of adjacent valleys at the second, distal position, each peak at the distal position being circumferentially adjacent to a valley at the proximal position.

116. The stent of claim 109, wherein:

adjacent peaks of the proximal ring being longitudinally aligned along the longitudinal axis of the stent; and adjacent valleys of the distal ring being longitudinally aligned along the longitudinal axis of the stent.

117. The stent of claim 109, wherein the ring length of each of the central rings being greater than the ring lengths of the proximal ring and the distal ring.

118. The stent of claim 109, further comprising straight links, wherein:

the valleys at the proximal position of the proximal ring and the circumferentially aligned peaks at the distal position of the distally adjacent central ring being coupled by straight links; and the peaks at the distal position of the distal ring and the circumferentially aligned valleys at the proximal position of the proximally adjacent central ring being coupled by straight links.

119. The stent of claim 109, wherein the undulating links having a plurality of curved portions with struts extending therebetween.

120. The stent of claim 119, wherein the struts of the undulating links including a straight configuration with the struts positioned perpendicular to the longitudinal axis of the stent.

121. The stent of claim 119, wherein the struts of the undulating links including a straight configuration with the struts positioned at an angle to the longitudinal axis of the stent.

122. The stent of claim 119, wherein the struts of the undulating links including a curved configuration.

123. The stent of claim 109, wherein the struts of the cylindrical rings including a straight configuration.

124. The stent of claim 109, wherein the struts of the cylindrical rings including a curved configuration.

125. The stent of claim 109, wherein at least a portion of the stent being coated with a drug.

126. The stent of claim 125, further comprising micro depots positioned along the undulating links and the links having straight portions and at least one curved portion at the outer surface of the stent, the drug substantially filling the micro depots.

127. The stent of claim 125, further comprising micro channels positioned along the undulating links and the links having straight portions and at least one curved portion at the outer surface of the stent, the drug substantially filling the micro channels.

128. The stent of claim 125, further comprising micro depots positioned along the proximal ring and the distal ring at the outer surface of the stent, the drug substantially filling the micro depots.

129. The stent of claim 125, further comprising micro channels positioned along the proximal ring and the distal ring at the outer surface of the stent, the drug substantially filling the micro channels.

130. The stent of claim 109, further comprising:

flexing portions, wherein at least some of the flexing portions having a nominal radial thickness; and stable portions, wherein at least some of the stable portions having a greater-than-nominal radial thickness.

131. The stent of claim 109, further comprising:

flexing portions, wherein at least some of the flexing portions having a nominal width; and stable portions, wherein at least some of the stable portions having a greater-than-nominal width.

132. An intravascular stent for use in a body lumen, comprising:

a plurality of cylindrical rings including a proximal ring, at least one central ring and a distal ring, each cylindrical ring having a strut pattern, a proximal end and a distal end, the proximal end and the distal end defining a ring length, the cylindrical rings being coaxially aligned along a common longitudinal axis forming the stent and radially expandable with a first delivery diameter and a second implanted diameter;

a plurality of undulating links coupling a plurality of adjacent cylindrical rings; and a plurality of links having straight portions and at least one curved portion coupling a plurality of adjacent cylindrical rings;

wherein each strut pattern of the cylindrical rings including an undulating pattern of U-shaped portions forming peaks at the proximal end of the cylindrical ring and valleys at the distal end of the cylindrical ring with struts extending therebetween;

the valleys of the proximal ring alternating between a single valley at a first, proximal position along the longitudinal axis of the stent and a pair of adjacent valleys at a second, distal position along the longitudinal axis of the stent;

the peaks of the at least one central ring alternating between a pair of adjacent peaks at a first, proximal position along the longitudinal axis of the stent and a single peak at a second, distal position along the longitudinal axis of the stent and valleys of the at least one central ring alternating between a single valley at a first, proximal position along the longitudinal axis of the stent and a pair of adjacent valleys at a second, distal position along the longitudinal axis of the stent, a peak at the first, proximal position being positioned between a pair of adjacent valleys at the second, distal position and a valley at the second, distal position being positioned between each pair of adjacent peaks at the first, proximal position, each peak at the distal position being circumferentially adjacent to a valley at the proximal position;

the peaks of the distal ring alternating between a pair of adjacent peaks at a first, proximal position along the longitudinal axis of the stent and a single peak at a second, distal position along the longitudinal axis of the stent;

the peaks positioned at the second, distal position being circumferentially aligned with the valleys positioned at the first, proximal position of the proximally adjacent cylindrical ring;

wherein the undulating links couple the peaks positioned at the second, distal position of a plurality of adjacent cylindrical rings to the circumferentially aligned valleys positioned at the first, proximal position on the proximally adjacent cylindrical rings; and wherein the links having the straight portions and at least one curved portion couple a plurality of adjacent cylindrical rings between valleys positioned between circumferentially adjacent pairs of peaks at the proximal position on one ring to the circumferentially aligned peaks positioned between a circumferentially aligned pair of valleys at the distal position on the proximally adjacent cylindrical ring.

133. The stent of claim 132, wherein a distal end of each undulating link being coupled to the apex of a peak positioned at the second, distal position on one cylindrical ring and a proximal end of the undulating link being coupled to the apex of the circumferentially aligned valley positioned at the first, proximal position on the proximally adjacent cylindrical ring.

134. The stent of claim 132, wherein a distal end of each undulating link being coupled a distance from the apex of a peak positioned at the second, distal position on one cylindrical ring and a proximal end of the undulating link being coupled a distance from the apex of the circumferentially aligned valley positioned at the first, proximal position on the proximally adjacent cylindrical ring.

135. The stent of claim 132, further comprising straight links, wherein:

straight links coupling the valleys at the first, proximal position of the proximal ring and the peaks at the second, distal position of the distally adjacent central ring; and straight links coupling the peaks at the second, distal position of the distal ring and the valleys at the first, proximal position of the proximally adjacent central ring.

136. An intravascular stent for use in a body lumen, comprising:

a plurality of cylindrical rings including a proximal ring, at least one central ring and a distal ring, each cylindrical ring having a strut pattern, a proximal end and a distal end, the proximal end and the distal end defining a ring length, the cylindrical rings being coaxially aligned along a common longitudinal axis forming the stent and radially expandable with a first delivery diameter and a second implanted diameter;

at least one undulating link coupling adjacent cylindrical rings; and at least one link having straight portions and at least one curved portion coupling adjacent cylindrical rings;

wherein in the second, implanted diameter of the cylindrical rings, the strut pattern of the cylindrical rings each include an undulating pattern of U-shaped portions forming peaks at the proximal end of the cylindrical ring and valleys at the distal end of the cylindrical ring with struts extending therebetween, the circumferential distance between adjacent peaks on the cylindrical rings being variable about the circumference of the cylindrical rings and the circumferential distance between adjacent valleys on the cylindrical rings being variable about the circumference of the cylindrical rings;

wherein between adjacent cylindrical rings, at least one peak on the distally adjacent ring is circumferentially aligned with a valley on the proximally adjacent cylindrical ring, at least one peak on the distally adjacent ring is circumferentially aligned with a peak on the proximally adjacent cylindrical ring, at least one valley on the distally adjacent ring is circumferentially aligned with a valley on the proximally adjacent cylindrical ring, and at least one valley on the distally adjacent ring is circumferentially aligned with a peak on the proximally adjacent cylindrical ring;

at least one undulating link coupling at least one pair of adjacent cylindrical rings between at least one peak on the distally adjacent cylindrical ring and the circumferentially aligned valley on the proximally adjacent cylindrical ring;

at least one link having the straight portions and at least one curved portion coupling at least one pair of adjacent cylindrical rings between at least one peak on the distally adjacent cylindrical ring and the circumferentially aligned peak on the proximally adjacent cylindrical ring;

at least one link having the straight portions and at least one curved portion coupling at least one pair of adjacent cylindrical rings between at least one valley on the distally adjacent cylindrical ring and the circumferentially aligned valley on the proximally adjacent cylindrical ring; and wherein at least one link having the straight portions and at least one curved portion couples at least one pair of adjacent cylindrical rings between at least one valley on the distally adjacent cylindrical ring and the circumferentially aligned peak on the proximally adjacent cylindrical ring.

137. The stent of claim 136, wherein:

between adjacent cylindrical rings, a plurality of peaks on the distally adjacent cylindrical ring being positioned at a first, proximal position and at least one peak on the distally adjacent cylindrical ring being positioned at a second, distal position;

between adjacent cylindrical rings, at least one valley on the proximally adjacent cylindrical ring being positioned at a first, proximal position and a plurality of peaks on the proximally adjacent cylindrical ring being positioned at a second, distal position; and the at least one peak at the second, distal position on the distally adjacent ring being circumferentially aligned with the at least one valley at the first, proximal position on the proximally adjacent ring.

138. The stent of claim 137, wherein the at least one undulating link coupling the at least one peak at the second, distal position on the distally adjacent ring to the circumferentially aligned valley at the first, proximal position on the proximally adjacent ring.

139. The stent of claim 136, wherein a distal end of each undulating link being coupled to the apex of the at least one peak on the distally adjacent cylindrical ring and a proximal end of the undulating link being coupled to the apex of the circumferentially aligned valley on the proximally adjacent cylindrical ring.

140. The stent of claim 136, wherein a distal end of each undulating link being coupled a distance from the apex of the at least one peak on the distally adjacent cylindrical ring and a proximal end of the undulating link being coupled a distance from the apex of the circumferentially aligned valley on the proximally adjacent cylindrical ring.

141. The stent of claim 140, wherein the distal end and proximal end of the undulating link being coupled to the same side of the respective apices of the peak and valley.

142. The stent of claim 140, wherein the distal end and proximal end of the undulating link being coupled to opposite sides of the respective apices of the peak and valley.

143. The stent of claim 136, wherein the curved portions of at least one of the links having straight portions and at least one curved portion are positioned between the adjacent cylindrical rings to which the link is coupled.

144. The stent of claim 136, wherein the curved portions of at least one of the links having straight portions and at least one curved portion are positioned between the struts of at least one of the adjacent cylindrical rings to which the link is coupled.

145. The stent of claim 136, wherein the ring length of each of the central rings being greater than the ring lengths of the proximal ring and the distal ring.

146. The stent of claim 136, further comprising straight links, wherein:
at least one valley of the proximal ring which is circumferentially aligned with a peak of the distally adjacent central ring being coupled by a straight link; and
at least one peak of the distal ring which is circumferentially aligned with a valley of the proximally adjacent central ring being coupled by a straight link.

147. The stent of claim 136, wherein the undulating links having a plurality of curved portions with struts extending therebetween.

148. The stent of claim 147, wherein the struts of the undulating links including a straight configuration with the struts positioned perpendicular to the longitudinal axis of the stent.

149. The stent of claim 147, wherein the struts of the undulating links including a straight configuration with the struts positioned at an angle to the longitudinal axis of the stent.

150. The stent of claim 147, wherein the struts of the undulating links including a curved configuration.

151. The stent of claim 136; wherein the struts of the cylindrical rings including a straight configuration.

152. The stent of claim 136, wherein the struts of the cylindrical rings including a curved configuration.

153. The stent of claim 136, wherein at least a portion of the stent being coated with a drug.

154. The stent of claim 153, further comprising micro depots positioned along the undulating links and the links having straight portions and at least one curved portion at the outer surface of the stent, the drug substantially filling the micro depots.

155. The stent of claim 153, further comprising micro channels positioned along the undulating links and the links having straight portions and at least one curved portion at the outer surface of the stent, the drug substantially filling the micro channels.

156. The stent of claim 153, further comprising micro depots positioned along the proximal ring and the distal ring at the outer surface of the stent, the drug substantially filling the micro depots.

157. The stent of claim 153, further comprising micro channels positioned along the proximal ring and the distal ring at the outer surface of the stent, the drug substantially filling the micro channels.

158. The stent of claim 136, further comprising:
flexing portions, wherein at least some of the flexing portions having a nominal radial thickness; and
stable portions, wherein at least some of the stable portions having a greater-than-nominal radial thickness.

159. The stent of claim 136, further comprising:
flexing portions, wherein at least some of the flexing portions having a nominal width; and
stable portions, wherein at least some of the stable portions having a greater-than-nominal width.

160. An intravascular stent for use in a body lumen, comprising:
a plurality of cylindrical rings including a proximal ring, at least one central ring and a distal ring, each cylindrical ring having a strut pattern, a proximal end and a distal end, the proximal end and the distal end defining a ring length, the cylindrical rings being coaxially aligned along a common longitudinal axis forming the stent and radially expandable with a first delivery diameter and a second implanted diameter;
a plurality of undulating links coupling a plurality of adjacent cylindrical rings; and
a plurality of links having straight portions and at least one curved portion coupling a plurality of adjacent cylindrical rings;
wherein in the second, implanted diameter of the cylindrical rings, the strut pattern of the cylindrical rings each including an undulating pattern of U-shaped portions forming peaks at the proximal end of the cylindrical ring and valleys at the distal end of the cylindrical ring with struts extending therebetween, the circumferential distance between adjacent peaks on the cylindrical rings being variable about the circumference of the cylindrical rings and the circumferential distance between adjacent valleys on the cylindrical rings being variable about the circumference of the cylindrical rings;
wherein between adjacent cylindrical rings, a plurality of peaks on the distally adjacent cylindrical ring being positioned at a first, proximal position and at least one peak on the distally adjacent cylindrical ring being positioned at a second, distal position, at least one valley on the proximally adjacent cylindrical ring being positioned at a first, proximal position and a plurality of peaks on the proximally adjacent cylindrical ring being positioned at a second, distal position, and the at least one peak at the second, distal position on the distally adjacent ring being circumferentially aligned with the at least one valley at the first, proximal position on the proximally adjacent ring;
wherein between adjacent cylindrical rings, at least one peak on the distally adjacent ring is circumferentially aligned with a peak on the proximally adjacent cylindrical ring, at least one valley on the distally adjacent ring is circumferentially aligned with a valley on the proximally adjacent cylindrical ring, and at least one valley on the distally adjacent ring is circumferentially aligned with a peak on the proximally adjacent cylindrical ring;
the undulating links coupling a plurality of pairs of adjacent cylindrical rings between the at least one peak at the second, distal position on the distally adjacent cylindrical ring and the circumferentially aligned valley at the first, proximal position on the proximally adjacent cylindrical ring;
the links having the straight portions and at least one curved portion coupling at least one pair of adjacent cylindrical rings between at least one peak on the distally adjacent cylindrical ring and the circumferentially aligned peak on the proximally adjacent cylindrical ring;
the links having the straight portions and at least one curved portion coupling at least one pair of adjacent cylindrical rings between at least one valley on the distally adjacent cylindrical ring and the circumferentially aligned valley on the proximally adjacent cylindrical ring; and
wherein the links having the straight portions and at least one curved portion couple at least one pair of adjacent cylindrical rings between at least one valley on the distally adjacent cylindrical ring and the circumferentially aligned peak on the proximally adjacent cylindrical ring.

161. The stent of claim 160, wherein a distal end of each undulating link being coupled to the apex of the at least one peak at the second, distal position on the distally adjacent cylindrical ring and a proximal end of the undulating link being coupled to the apex of the circumferentially aligned valley at the first, proximal position on the proximally adjacent cylindrical ring.

162. The stent of claim 160, wherein a distal end of each undulating link being coupled a distance from the apex of the at least one peak at the second, distal position on the distally adjacent cylindrical ring and a proximal end of the undulating link being coupled a distance from the apex of the circumferentially aligned valley at the first, proximal position on the proximally adjacent cylindrical ring.

163. The stent of claim 162, wherein the distal end and proximal end of at least one undulating link being coupled to the same side of the respective apices of the peak and valley.

164. The stent of claim 162, wherein the distal end and proximal end of at least one undulating link being coupled to opposite sides of the respective apices of the peak and valley.

165. The stent of claim 160, wherein the curved portions of at least one of the links having straight portions and at least one curved portion are positioned between the adjacent cylindrical rings to which the link is coupled.

166. The stent of claim 160, wherein the curved portions of at least one of the links having straight portions and at least one curved portion are positioned between the struts of at least one of the adjacent cylindrical rings to which the link is coupled.

167. The stent of claim 160, further comprising straight links, wherein:
at least one valley of the proximal ring which is circumferentially aligned with a peak of the distally adjacent central ring being coupled by a straight link; and
at least one peak of the distal ring which is circumferentially aligned with a valley of the proximally adjacent central ring being coupled by a straight link.

168. An intravascular stent for use in a body lumen, comprising:
a plurality of cylindrical rings including a proximal ring, at least one central ring and a distal ring, each cylindrical ring having a strut pattern, a proximal end and a distal end, the proximal end and the distal end defining a ring length, the cylindrical rings being coaxially aligned along a common longitudinal axis forming the stent and radially expandable with a first delivery diameter and a second implanted diameter; and
a plurality of links having straight portions and at least one curved portion coupling adjacent cylindrical rings;
wherein in the second, implanted diameter of the cylindrical rings, the strut pattern of the cylindrical rings each include an undulating pattern of U-shaped portions forming peaks at the proximal end of the cylindrical ring and valleys at the distal end of the cylindrical ring with struts extending therebetween, the circumferential distance between adjacent peaks on the cylindrical rings being variable about the circumference of the cylindrical rings and the circumferential distance between adjacent valleys on the cylindrical rings being variable about the circumference of the cylindrical rings;
at least one link coupling at least one pair of adjacent cylindrical rings between at least one peak on the distally adjacent cylindrical ring and a circumferentially nonaligned valley on the proximally adjacent cylindrical ring;
at least one link coupling at least one pair of adjacent cylindrical rings between at least one peak on the distally adjacent cylindrical ring and a circumferentially nonaligned peak on the proximally adjacent cylindrical ring;
at least one link coupling at least one pair of adjacent cylindrical rings between at least one valley on the distally adjacent cylindrical ring and a circumferentially nonaligned valley on the proximally adjacent cylindrical ring; and
wherein at least one link couples at least one pair of adjacent cylindrical rings between at least one valley on the distally adjacent cylindrical ring and a circumferentially nonaligned peak on the proximally adjacent cylindrical ring.

169. The stent of claim 168, wherein the curved portions of the links are positioned between the adjacent cylindrical rings to which the link is coupled.

170. The stent of claim 168, wherein the ring length of each of the central rings being greater than the ring lengths of the proximal ring and the distal ring.

171. The stent of claim 168, wherein the struts of the cylindrical rings including a straight configuration.

172. The stent of claim 168, wherein the struts of the cylindrical rings including a curved configuration.

173. The stent of claim 168, wherein at least a portion of the stent being coated with a drug.

174. The stent of claim 173, further comprising micro depots positioned along the undulating links and the links having straight portions and at least one curved portion at the outer surface of the stent, the drug substantially filling the micro depots.

175. The stent of claim 173, further comprising micro channels positioned along the undulating links and the links having straight portions and at least one curved portion at the outer surface of the stent, the drug substantially filling the micro channels.

176. The stent of claim 173, further comprising micro depots positioned along the proximal ring and the distal ring at the outer surface of the stent, the drug substantially filling the micro depots.

177. The stent of claim 173, further comprising micro channels positioned along the proximal ring and the distal ring at the outer surface of the stent, the drug substantially filling the micro channels.

178. The stent of claim 168, further comprising:
flexing portions wherein at least some of the flexing portions having a nominal radial thickness; and
stable portions, wherein at least some of the stable portions having a greater-than-nominal radial thickness.

179. The stent of claim 168, further comprising:
flexing portions, wherein at least some of the flexing portions having a nominal width; and
stable portions, wherein at least some of the stable portions having a greater-than-nominal width.

* * * * *